(12) United States Patent
Chen

(10) Patent No.: US 7,851,152 B2
(45) Date of Patent: Dec. 14, 2010

(54) FLUORESCENT BASE ANALOGUES' USAGE IN THE CHARACTERIZATION OF NUCLEIC ACID MOLECULES AND THEIR INTERACTIONS

(76) Inventor: Yaodong Chen, 648 Pegasus Ln., Foster City, CA (US) 94404

( * ) Notice: Subject to any disclaimer, the term of this patent is extended or adjusted under 35 U.S.C. 154(b) by 658 days.

(21) Appl. No.: 11/234,762

(22) Filed: Sep. 23, 2005

(65) Prior Publication Data

US 2008/0020378 A1   Jan. 24, 2008

Related U.S. Application Data

(60) Provisional application No. 60/612,672, filed on Sep. 25, 2004.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | |
|---|---|---|---|
| 5,525,711 A * | 6/1996 | Hawkins et al. | 536/22.1 |
| 5,723,591 A * | 3/1998 | Livak et al. | 536/22.1 |
| 5,763,167 A * | 6/1998 | Conrad | 435/6 |
| 5,912,146 A * | 6/1999 | Nishimura et al. | 435/91.1 |
| 5,925,517 A * | 7/1999 | Tyagi et al. | 435/6 |
| 6,022,686 A * | 2/2000 | Garman et al. | 435/6 |
| 6,451,530 B1 * | 9/2002 | Hawkins | 435/6 |
| 6,716,971 B1 * | 4/2004 | Hawkins et al. | 536/23.1 |
| 6,743,586 B2 | 6/2004 | Marino et al. | |
| 6,811,973 B1 * | 11/2004 | Reich | 435/6 |
| 7,198,900 B2 * | 4/2007 | Woudenberg et al. | 435/6 |
| 7,232,691 B2 * | 6/2007 | Kraus et al. | 436/526 |
| 2001/0049434 A1 * | 12/2001 | Conklin | 536/23.1 |
| 2002/0102577 A1 * | 8/2002 | Raillard et al. | 435/6 |
| 2002/0127593 A1 * | 9/2002 | Reich et al. | 435/6 |
| 2003/0165846 A1 * | 9/2003 | Marino et al. | 435/6 |
| 2003/0180746 A1 * | 9/2003 | Kmiec et al. | 435/6 |
| 2004/0009933 A1 * | 1/2004 | Wise et al. | 514/43 |
| 2004/0110213 A1 * | 6/2004 | Namsaraev | 435/6 |
| 2005/0176940 A1 * | 8/2005 | King | 536/23.1 |
| 2007/0238096 A1 * | 10/2007 | Reich et al. | 435/5 |

FOREIGN PATENT DOCUMENTS

| WO | WO 95/31469 | * 11/1995 |
|---|---|---|
| WO | WO98/26093 | * 6/1998 |

OTHER PUBLICATIONS

Marquez et al., Using 2-Aminopurine fluorescencce and mutational analysis to demonstrate an active role of bacteriophage T4 DNA polymerasde in strand separation required for 3' → 5' -exonuclease activity. Journal of Biological Chemistry 46(15) : 28,903-28,911 (1996).*

Gene Characterization Kits ; The Stratagene Catalog p. 39 (1988).*

Berry et al. Pyrrolo-dC and pyrrolo-C: fluorescent analogs of cytidine and 2'-deoxycytidine for the study of oligonucleotides. Tetrahedron Letters 45(11), 2457-2461 (2004).*

Bloom et al. Influence of 5'-nearest neighbors on the insertion kinetics of the fluorescent nucleotide analog 2-aminopurine by Klenow fragment. Biochemistry 32(41) : 11247-11258 (1993).*

Driscoll et al. Fluorescence properties of a new guanosine analog incorporated into small oligonucleotides. Biophysical Journal, vol. 73, No. 6, pp. 3277-3286 (1997).*

Eritja et al, Synthesis and properties of defined DNA oligomers containing base mispairs involving 2-aminopurine. Nucleic Acids Research 14 :869-5884 (1986).*

Hawkins et al. Fluorescence properties of pteridine nucleoside analogs as monomers and incorporated into oligonucleotides. Analytical Biochemistry vol. 244, No. 1, pp. 86-95 (1997).*

Hawkins, Synthesis and fluorescence characterization of pteridine adenosine nucleoside analogs for DNA incorporation. Analytical Biochemistry 298 (2) : 231-240 ( 2001).*

Hawkins et al., Incorporation of a fluorescent guanosine analog into oligonucleotides and its application to a real time assay for the HIV-1integrase 3'-processing reaction. Nucleic Acids Research 23 ( 15): 2872-80 (1995).*

Hawkins, M. Fluorescent pteridine nucleoside analogs: A window on DNA interactions. Cell Biochemistry and Biophysics 34 ( 2) : 257-281 (2001).*

Holmen et al., Electronic transition moments of 2-aminopurine. Journal of the American Chemical Society 119(13), 3114-3121 (1997).*

Kourentzi et al.,Hybridization-responsive fluorescent DNA probes containing the adenine analog 2-aminopurine. Analytical Biochemistry 322 : 124-126 (2003).*

(Continued)

Primary Examiner—Ethan Whisenant

(57) ABSTRACT

This invention provides methods, apparatus and kits for the quantitative and qualitative characterization of the nucleic acid molecule's behavior by modify the nucleic acid molecules to incorporate selected fluorescent base analogues (FBAs). The methods generally place one or more fluorescent base analogue into a nucleic acid molecule (e.g., an oligonucleotide) to replace the corresponding normal base(s), arrange fluorescent base analogues as intrinsic fluorescent probes by using direct excitation, indirect excitation, and excimer emission labeling schemes, introducing so modified nucleic acid molecules into the matrix with interested condition and measuring the fluorescent properties of the modified nucleic acid molecules at the specific emission wavelength of FBA(s). The apparatus is designed to irradiate the FBA(s) incorporated nucleic acid molecule at a wavelength in the range of 240 nm-280 nm and detect the fluorescent activities at the specific emission wavelength of the respective FBA(s). The kit provides oligonucleotides modified by multiple FBAs in the position of critical portions. It utilizes simultaneous indirect excitation labeling scheme for qualitative and quantitative investigation of nucleic acid molecules' interaction in vitro and in vivo.

8 Claims, 10 Drawing Sheets

OTHER PUBLICATIONS

Lycksell et al. Base pair opening dynamics of a 2-aminopurine substituted Eco RI restriction sequence and its unsubstituted counterpart in oligonucleotides. Nucleic Acids Research 15 (21): 9011-9025 (1987).*

Rist et al., Fluorescent Nucleotide Base Analogs as Probes of Nucleic Acid Structure, Dynamics and Interactions. Current Organic Chemistry 6 :775-793 (2002).*

Sandin et al., Synthesis and oligonucleotide incorporation of fluorescent cytosine analogue tC: a promising nucleic acid probe, Nature Protocols 2, 615-623 (2007).*

Stivers J.T., 2-Aminopurine fluorescence studies of base stacking interactions at abasic sites in DNA : metal-ion and base sequence effects. Nucleic Acids Research vol. 26, No. 16, pp. 3837-3844 (1998).*

Ward et al., Fluorescence studies of nucleotides and polynucleotides. I. Formycin, 2-aminopurine riboside, 2,6-diaminopurine riboside, and their derivatives. The Journal of Biological Chemistry, 244 (5) : 1228-37 (1969).*

Shchyolkina et al., Formation of an intramolecular triple-stranded DNA structure monitored by fluorescence of 2-aminopurine or 6-methylisoxanthopterin. Nucleic Acids Res. Jan. 22, 2004;32(2):432-40 (Jan. 2004).*

Uchiyama et al. Detection of undegraded oligonucleotides in vivo by fluorescence resonamnce energy transfer. Journal of Biological Chemistry 271 (1) : 380-384 (1996).*

Xu et al., Sequence Dependence of energy transfer in DNA oligonucleotides. Biophysical Journal 78 : 1042-1058 (2000).*

Jean et al., 2-Aminopurine fluorescence quenching and lifetimes : Role of base stacking. PNAS 98 (1) : 37-41 (2001).*

Nordlund et al., Excitation Energy Transfer in DNA : Duplex melting and transfer from normal bases to 2-aminopurine. Biochemistry 32 : 12090-12095 (1993).*

Aoki et al., The Fluorescence of Native DNA at Room Temperature. Chem. Phys. Letters., 92 : 327-332 (1982).*

Burr et al. Energy transfer in fluorescent derivatives of uracil and thymine. JACS 97 : 245-248 (1975).*

Ge et al. Excited-state properties of the alternating polynucleotide poly(dA-dT) • poly(dA-dT). Photochem. Photobiol. 54 : 301-305 (1991a).*

Ge et al. Room-temperature fluorescence properties of the polynucteotide polydA • polydT. Photochem. PhotobioL 54:477-480 (1991b).*

Gueron et al., Excited states of nucleotides and singlet energy transfer in polynucleotides. J. Chem. Phys. 47 : 4077-4091 (1967).*

Holz et al., 2-Aminopurine as a fluorescent probe for DNA base flipping by methyltransferases. Nucleic Acids Research 26 : 1076-1083 (1998).*

Huang et al.., Room-temperature steady-state fluorescence properties of poly(dG-dC) • poly(dG—dC). Photochem. Photobiol. 56 : 95-99 (1992).*

Kelley et al., Electron transfer between bases in double helical DNA Science 283 :375-381 (1999).*

Nordlund et al. Structural dynamics of DNA sensed by fluorescence from chemically-modified bases. Proc. SPIE. 1204 : 344-353 (1990).*

A. K. Shchyolkina, etal. Formation of an Intramolecular Triple-Stranded DNA Structure Monitored by Fluorescence of 2-aminopurine or 6-methylisoxanthopterin, Nucleic Acid Research, 2004, vol. 32, No. 2, 432-440.

D. Xu & T.M. Nordlund, Sequence Dependence of Energy Transfer in DNA Oligonucleotides. Biophysical Journal, Feb. 2000, vol. 78 1042-1058.

H. Uchiyama et al. Detection of Undegraded Oligonucleotides in Vivo By Fluorescence Resonance Energy Transfer. Journal of Biological Chemistry Jan. 1996, vol. 271, No. 1, 380-384.

* cited by examiner

| Normal Base | Fluorescent Analog (deoxy)Ribonucleoside | Excitation Wavelength | Emission Wavelength |
|---|---|---|---|
| Adenine  | 2-aminopurine  | 310nm | 350nm -380nm peak at 370nm |
| | 4-amino-6-methyl-pteridone  | 330nm | 410nm -450nm peak at 435nm |
| Guanine  | 6-methyl-isoxanthopterin  | 340nm | 410nm -450nm peak at 430nm |
| Cytosine  | Pyrrolo-(d)C  | 350nm | 440nm-480nm peak at 460nm |

FLUORESCENT BASE ANALOGUES' USAGE IN THE CHARACTERIZATION OF NUCLEIC ACID MOLECULES AND THEIR INTERACTIONS

CROSS-REFERENCE TO RELATED APPLICATIONS

This application claims the benefit of the prior filing date of the provisional patent application:
Title: Fluorescent Base Analogues' Usage in the Pharmacokinetic and Pharmacodynamic Detection of Nucleic acid drugs
Inventor: Yaodong Chen
Application No. 60/612,672
Filing Date Sep. 25, 2004
The above provisional application is hereby incorporated by reference for all the purpose.

FIELD OF THE INVENTION

This invention is in the field of nucleic acid's conformation and structure determination by detecting the fluorescent activity of the fluorescent base analogue(s) incorporated. It provides methods, apparatus and kits for the quantitative and qualitative characterization of the so modified nucleic acid molecule's behavior under the influence of its environment.

BACKGROUND OF THE INVENTION

Investigations on the dynamic structural and conformational change of nucleic acid may reveal its interaction with environment at molecular level. This invention provides a powerful method, unique apparatus and convenient kits for the investigation of the structure and conformation of these nucleic acid molecules in real time. The methods in this invention transform the nucleic acid molecule into its own fluorescent probe and force it to reveal its interactions with other nucleic acids, proteins and biomolecules or complexes in vitro and in vivo.

Generally, nucleic acid molecules under study are chemically synthesized oligo(deoxy)nucleotides or oligonucleotides. In this invention, oligonucleotides (ON) is used for the general discussions concerning nucleic acid study.

1) Fluorescent Base Analogues as Nucleic Acid Molecule's Intrinsic Probe

Since the ON molecules under study have the same nucleotides with the nucleic acids molecules in the biological matrix, the former approaches to the detection of these molecules have to use extrinsic probes. Current approaches for the detection of nucleic acid molecules' structure and interactions typically rely on fluorescence resonance energy transfer (FRET) between a fluorophore and a quencher molecule or a second fluorophore (e.g., a fluorescence resonance energy transfer system). Two fluorophores are attached to different nucleic acids. FRET occurs when the two fluorophores are brought into proximity under exciting radiation. The direct correlation of measurable FRET efficiency with the distance between the two chromophores has made FRET one of the most extensively used methods to investigate molecular interactions. A reversed approach is called molecular beacon. It utilizes nucleic acid probes bearing a fluorophore and a quencher molecule. The probes were self-complementary and adopted a hairpin conformation in solution. The hairpin juxtaposed the fluorophore and the quencher thereby reducing or eliminating fluorescence of the fluorophore. When the probes hybridized to a target nucleic acid, they unfold into linear conformation, thus separate the fluorophore from the quencher molecule and reveal a detectable fluorescent signal.

Both of these approaches required an extrinsic fluorescent probe and a second fluorophore or a quencher. Most extrinsic fluorescent probes and their binding moieties are relatively large. The presence of bulky fluorescent labels and associated linkers not only alter the mobility of the nucleic acid but also change the interaction of the nucleic acid so labeled with other molecules either through chemical interactions or through steric hindrance. Therefore, the use of these extrinsic markers in the study of nucleic acid molecule may not reflect its real behavior.

This invention utilizes fluorescent base analogue substitutions serving as intrinsic probes. Representative fluorescent base analogues are presented in FIG. 1. A major feature of these base analogues is that they are designed as structural analogs to the natural bases to minimize the perturbation of the formation of helix and normal interaction with enzymes other biomolecules. They exhibit much higher fluorescence quantum yields than the natural bases. Like in natural nucleosides, they are incorporated into the oligonucleotide through a (deoxy)ribose linkage. Some of them have been produced as phosphoramidites, therefore they can be site-specifically incorporated into DNA using automated DNA synthesis. Their fluorescence intensities are very sensitive to the conformational change and binding situations, therefore are suitable as probes in characterization of nucleic acid molecule's behavior.

In this invention, one or several fluorescent base analogue(s) is (are) substituted into the nucleic acid molecule to replace the corresponding biological base(s). The substituting fluorescent base in the nucleic acid sequence serves as intrinsic fluorescent probe to facilitate comprehensive characterization of nucleic acid molecule' behavior under the influence of the medium or matrix. The methods generally substitute one or more fluorescent base analogue into a nucleic acid (e.g., an oligonucleotide) to replace the corresponding normal base(s) and test its fluorescent properties under the target condition. The substitution of the fluorescent base analogues within the nucleic acid sequence renders them exquisitely sensitive to changes in conformation and integrality as the nucleic acid meets and reacts with other molecules. Subtle structural and conformational changes, like bending, annealing, binding, digestion or cleavage of these fluorescent base analogues-containing nucleic acid molecules can be detected by monitoring changes in fluorescence properties, such as the fluorescence intensity, anisotropy, lifetimes, spectral shifts, and energy transfer characteristics.

2) Fluorescence Properties of Fluorescent Base Analogues

Fluorescence spectroscopy has the advantage of high detection capability, high selectivity and high sensitivity to intermolecular interactions. The following fluorescence properties may be used to characterize the nucleic acid molecule:
  Excitation wavelength
  Excitation absorbance
  Emission wavelength
  Fluorescence intensity
  Energy transfer efficiency
  Fluorescence Lifetime
  Anisotropy Three new findings of the properties of the incorporated fluorescent base analogues serve as the theoretical foundation of this invention:

1. The modulation of fluorescence properties of the incorporated fluorescent base analogue may be directly correlated to the structure change and interaction feature of the nucleic acid molecule so modified.
2. Sequence dependent energy transfer inside nucleic acid molecule is generally feasible between the normal bases and well designed fluorescent base analogues;
3. Juxtapositioned identical fluorescent bases in the nucleic acid sequence may form dimmer and have pronounced excimer fluorescent emissions.

Fluorescence activity of a fluorophor may be quenched as a result of interaction of either the ground or excited state of the other species in solution. Interaction between the quencher and the excited fluorophore is called dynamic or collisional quenching; relatively stable complex formed between the quencher and the potentially fluorescent species in the ground state is called static quenching. Although both of these quenching mechanisms influence the fluorescence emission of the base analogues, the static quenching is more pronounced for fluorescent bases incorporated into the nucleic acid molecules. Staked in the sequence, base analogues' fluorescence may be substantially quenched up to 90%. It has been discovered that the disturbance of the stacking position of the fluorescent bases may reduce or eliminate the quenching and recover the quenched fluorescence in some level depending on the interaction with other molecules. For example, if the substituted base analogue is flipped out by enzyme interaction into open environment, the fluorescent may be fully recovered; if repairing enzymes excise or replace the substituted base analogues, their fluorescence activity will be restored to their free monomer level. This recovery may result in more than 10-fold increase of fluorescence from the quenched stacking configuration.

It is further found that, as a general phenomenon, the pronounced fluorescence of the base analogues in aqueous environment will be quenched when it is incorporated into a more hydrophobic condition, such as hybridization into double helix, bound as a substrate into an enzyme, or enveloped into cellular organelles. The fluorescence of single strand nucleic acid molecule, or even double strand nucleic acid molecule may be further reduced by these kinds of hydrophobic bindings. Thus, the change of fluorescence properties of the nucleic acid molecule with substituted fluorescent base analogue may characterize the interaction of the nucleic acid molecule in a qualitative manner.

Energy migration along the DNA bases has attributed to the DNA lesions far from the absorbing site. It has been discovered that, excited normal bases may transfer their energy to the adjacent fluorescent base analogues, and excite them for fluorescence emission. This phenomenon is different from the fluorescence resonance energy transfer (FRET). FRET is a comparatively long-range phenomenon. In FRET, the excitation of the donor results the fluorescence emission, which has to be in the excitation range of the acceptor. If nearby acceptor is in the parallel transition dipole orientation, it will become excited and subsequently undergoes the same physical and chemical processes as if excited directly. However, Energy transfer in DNA or RNA is believed to be electron exchange or charge transfer. It doesn't need donor's fluorescence emission to excite the acceptor like in FRET, but it requires some overlap of the electron orbitals of the excited donor and the acceptor. Instead of the relatively long-range interaction in FRET (10-100 Angstroms), energy transfer in DNA/RNA needs much closer proximity and more precise orientation. It is a discovery of this invention that, DNA/RNA's adjacent base distance (3.4-3.6 Angstroms) and base stacking arrangement make this kind of intrasequence energy transfer generally available for structurally similar base analogues.

This invention utilizes the intrasequence energy transfer from normal bases to fluorescent base analogues to serve as indirect excitation of the fluorescent analogues. This method ties the fluorescent emission of the base analogues to the normal bases, thus it is more sensitive to the structural and conformational change of the whole nucleic acid molecule.

The aggregation of an excited-state molecule with a ground state molecule produces an excited state complex ("exciplex"). A special case of exciplexes occur if the excited-state and ground-state molecules are of the same kind, which is then called an excited state dimer ("excimer"). This species is a charge-transfer complex that is held together by favorable orbital interactions as well as by Coulombic binding forces. Exciplexes are distinct intermediates in their own right and possess unique properties. For instance, their fluorescence excitation and emission is almost always at longer wavelengths (lower energy level) than that of the excited state. This short-range phenomenon is only significant when the electron orbitals of donor and acceptor overlap. It is most efficient when the exciplexes formed by the same kind of molecules. Therefore, excimer is the most favored case in exciplex phenomena.

In general, the close proximity and precise spatial stacking of nucleotide in sequence facilitates excimer formation. If identical base analogues are put into nucleic acid molecule at adjacent positions, intramolecular base excimer may forms from the excitation of ground state dimerization, or from the relaxation of the excited individual bases. Although the fluorescence of excimer is weaker, its red-shifted wavelength and sensitivity may be used for nucleic acid molecule conformation detection. In addition to the binding sensitivity common for other labeling arrangement, the excimer formation delicately depends on the stacking of the adjacent bases. If the base stacking were disturbed, the fluorescence of the excimer will decrease or disappear.

This invention makes use of excimer fluorescent emission to facilitate another way to tie the fluorescence signal of the base analogues with the whole nucleic acid molecules. It is especially suitable for structural change detection of double strand oligonucleotides. Excimer formation in nucleic acid also generates a fluorescent signal in the further red shift of the cell auto-fluorescence range. The longer wavelength emission by the excimer further distinguishes the signal from background fluorescence of the biological matrix of the nucleic acid molecules, thus makes the measurement more reliable.

In summary, this invention provides a novel method, corresponding apparatus and kits to make quantitative and qualitative investigation of nucleic acid molecules' structure and interaction. By using fluorescent base analogues as intrinsic probes, this invention ties the fluorescent base analogues within the nucleic acid sequence and transforms the nucleic acid molecule into a fluorescent probe of itself to demonstrate its behavior in real time.

SUMMARY OF THE INVENTION

This invention provides new methods, apparatus and compositions for the characterization of nucleic acid molecules. It utilizes fluorescent base analogs as intrinsic fluorescent probes in such a way to facilitate the reliable detection of the structure and activity of the nucleic acid molecule in vitro and in vivo.

The methods of this invention generally includes placing or substituting one or more fluorescent base analogues into an nucleic acid molecule, introducing so modified nucleic acid molecules into the matrix with interested condition and measuring the fluorescent properties of the introduced nucleic acid molecules. The detected fluorescence properties reveal the structure and conformation change and therefore, the activity of the nucleic acid molecules under the interaction and influence of the matrix.

In one kind of embodiments, one or several nucleoside bases in the nucleic acid molecule is/are substituted by corresponding fluorescent analogs. In some preferred embodiments, multiple base analogues are substituted into separate positions. In some other embodiments, different kinds of fluorescent bases are substituted into different interested sections of the nucleic acid molecule. In particularly preferred embodiments, the fluorescent bases are present at both end and middle sections. These modified nucleic acid molecules are then introduced into the medium of interest and their fluorescent properties are detected by measuring the fluorescence emission of the respective base analogues.

In another kind of embodiments, substituting fluorescent bases in the nucleic acid molecule are indirectly excited via the excitation of the normal base as their energy donor. In some preferred embodiments, fluorescent base analogues are substituted into the corresponding base with the flanking natural bases. In other preferred embodiments, multiple different base analogues are substituted into separate positions and simultaneously excited by radiation of the normal bases at a wavelength in the ranged of 240-280 nm.

In still another kind of embodiments, multiple identical nucleotides in adjacent positions are substituted by identical corresponding fluorescent base analogues. The modified nucleic acid molecules are then introduced into the matrix of interest and their fluorescent properties are measured by excimer excitation and emission.

In all of above embodiments, the fluorescent base analogues include one or more of the fluorescent base analogues described in FIG. 2.

This invention also provides an apparatus and kits for the application of this invention. The apparatus in this invention is a specialized equipment for fluorescence detection of the fluorescent base analogue modified nucleic acids with unique excitation and emission wavelength settings. The kit can comprise sets of fluorescent oligo(deoxy)nucleotides incorporating the base analogues described herein in short sequence for enzyme kinetic study, DNA/RNA drug delivery system testing and nuclei acid damaging agent screening. The kit can further comprise a buffer, and/or any of the other reagents useful for practicing the method to which the kit is directed.

ABBREVIATIONS AND DEFINITIONS

1) Abbreviations
The following abbreviations are used in this application:
A: adenine
C: cytosine
DNA: deoxyribonucleic acid
dsDNA: double-stranded DNA
FBA: fluorescent base analogue
G: guanine
ON: oligo(deoxy)nucleotide
PK/PD: Pharmacokinetic and Pharmacodynamic
QY: quantum yield
RNA: ribonucleic acid
ssDNA: single-stranded DNA
T: thymine
U: uracil 2) Definitions
In some of the cases, nucleic acid studies are conducted by using DNA or RNA oligonucleotide (ON), which range in length from 2 to 200 bases. It is well known that oligonucleotides may be ligated together to provide longer sequences. The term "oligonucleotide" also encompasses these longer sequences. It is also recognized that double-stranded polynucleotides may be created by hybridization with a complementary sequence or enzymatically through primer extension. ON, as used hereafter, refers to a molecule comprised of two or more deoxyribonucleotides, ribonucleotides, modified ribonucleotides, modified deoxyribonucleotides, fluorescent or non-fluorescent ribonucleotide analogues, or fluorescent or non-fluorescent deoxyribonucleotide analogs in their single or double-strand. It also includes the ON molecules modified in their backbone structure.

The term "Quantum Yield" (QY), as used herein, in fluorescence spectroscopy is normally defined as the ratio of the number of photons emitted to the number of the photons absorbed by the fluorophore.

The term "quenching", as used herein, refer to any process that decreases the fluorescence intensity of a sample (e.g. excited-state reactions, molecular rearrangements, energy transfer or charge transfer) is called quenching.

The terms "base", as used herein, refer to the "standard" ribonucleotide bases or deoxyribonucleotide bases: adenine, guanine, cytosine, thymine, and uracil, or derivatives of these bases. Such derivatives include, but are not limited to, inosine, 5-bromocytsiine, 5-bromo-uracil, 6-methyl-adenine and 5-methyl-cytosine. The terms also include base analogues, more preferably fluorescent base analogues including, but not limited to 2-aminopurine and any of the other fluorescent nucleotides disclosed herein.

A "fluorescent base" or a "fluorescent base analogue" or "base analogue" as used herein, refers to a base analogue that is capable of emitting a fluorescent signal when illuminated with light of an appropriate wavelength. It includes any base analogue emits a fluorescent signal when it exist in a nucleotide monomer in an aqueous solution.

The term "fluorescent oligonucleotide" or "labeled oligonucleotides", as used herein, refers to an oligonucleotide incorporating one or more fluorescent base analogues.

The term "corresponding base/nucleotide", is used to refer the normal base/nucleotide in a nucleic acid to which the fluorescence base/nucleotide make a structural analogy. Thus, a corresponding base/nucleotide refers to a base/nucleotide that may be substituted by the fluorescent analog without substantial change of its chemical property.

"Hybridization" refers to the specific binding of two nucleic acids through complementary base pairing. Hybridization typically involves the formation of hydrogen bonds between nucleotides in one nucleic acid and their complementary nucleotides in the second nucleic acid.

The phrase "stable binding", refers to the nucleic acid molecule's binding to proteins, complexing to other biomolecules, or hybridizing with a particularly nucleotide sequence or subsequence in the interested matrix.

The term "complementary base pair" refers to a pair of bases (nucleotides) each in a separate nucleic acid in which each base of the pair is hydrogen bonded to the other. A "classical" (Watson-Crick) base pair always contains one purine and one pyrimidine: adenine pairs specifically with thymine (A-T), guanine with cytosine (G-C), uracil with adenine (U-A). The two bases in a classical base pair are said to be complementary to each other.

DETAILED DESCRIPTION

This invention provides methods of detection of nucleic acid molecules' structural change and their interaction with other molecules. The methods involve placing or substituting one or multiple bases of a nucleic acid molecule with their fluorescent base analogue(s), introducing said modified nucleic acid molecule into the medium studied, such as, but not limited by, in vitro media, culture cell, tissue sample, circulating blood system, or in situ living tissues, and measuring the fluorescence properties, such as the excitation wavelength, emission wavelength, excitation absorbance, emission intensity, energy transfer efficiency, life-time and anisotropy, produced by the incorporated fluorescent nucleotide(s) under the interactions within the medium. The invention also provides an apparatus and kits for the usage of the method.

This invention's use of the fluorescent analogues is a novel method of real-time investigation of the structure and conformation of the nucleic acid molecules under the multi-aspects influence from the matrix, in which they are introduced. The invention is fully disclosed in the following sections.

1. Fluorescent Base Analogs Screening:

Fluorescence is a highly sensitive technique that is able to report on relatively local interactions. Although the naturally occurring nucleotide bases (guanine (G), adenine (A), thymine (T), uracil (U) and cytosine (C)) in DNA and Uricil (U) in RNA) absorb UV/vis radiation well, their intrinsic fluorescence is almost non-existent. These bases exhibit very short fluorescent decay times, generally in the range of a few picoseconds, and do not provide much structural information since signals are normally averaged over all bases in the nucleic acid sequence. Thus, in contrast to proteins, RNA and DNA molecules in general lack naturally occurring intrinsic fluorescent reporters.

This invention turns the above drawbacks into advantage by using fluorescent nucleotide base analogs (FBA) with better fluorescence properties (i.e. higher quantum yields and longer lifetimes) and the convenience of standard automated synthetic methods. Since no substantial fluorescence of the natural bases is present, the substituting fluorescent base analogue for a normal base may serve as a pseudo intrinsic probe without competing background signals.

Figure 1:
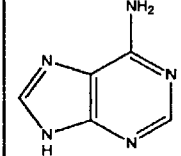
FIG. 1: Nucleoside and its fluorescent analogues, which may be prepared as phosphoramidites.

Several fluorescent nucleoside analogues have been prepared as phosphoramidites in recent years. (See FIG. 1) These promising analogues include the adenosine analogue, such as 2-Aminopurine, 2,6-diaminopurine, formycin, 4-amino-6-methyl-pteridone, and etheno-A; guanine analogues, such as 6-methyle-isoxanthopterin, 3-methyl-isoxanthopterin, and isoxanthopterin; cytosine analogues, such as pyrrolo-(d)C, and 5-(1-pyrenylethynyl)-(d)C; thymine analogues, like furano-(d)T and isoxanthine; uricil analogues, like 5-(1-pyrenylethynyl)-U, benzo-U and lumazine. By definition, a base analog is not an exact replacement for the physiological corresponding base that it replaces. Etheno-A and etheno-C are two readily accessible fluorescent structures but these molecules are both non-hybridizing; furano-T is unstable during synthesis steps. Of the fluorescent base analogues described here, 5-(1-pyrenylethynyl)-(d)C/U introduces steric bulk in the major groove. 3-MI, a pteridine derivative, places a methyl group at the Watson-Crick interface, leading to duplex destabilization. Satisfyingly, most of these fluorescent base analogues have only a minor effect on duplex stability.

For probing nucleic acid molecule's conformation and structure change, the ideal fluorescent nucleoside analog should display high fluorescence intensity that is sensitive to its microenvironment, and a large Stokes shift; it should be stable during continued illumination; it should be amenable to phosphoramidite preparation for incorporation into oligonucleotides by automated synthesis; it should be non-perturbing to the process being observed; it should behave as a regular nucleoside in its interaction with proteins and enzymes; and it should be capable of being converted to the triphosphates and be incorporated into DNA with high efficiency by current commercial polymerases.

In some embodiments, preferred fluorescent base analogues may include 2-aminopurin (2-AP) and 4-amino-6-methyl-pteridone (6-MAP) for adenine, 6-methyl-isoxanthopterin for guanine, pyrrolo-(d)C (py-C) for cytosine. Excitation maximum and the emission maximum of these selected base analogues are given FIG. 2.

2AP is a fluorescent analogue of adenosine (6-aminopurine). As a nucleotide base analog, 2AP is incorporated in DNA/RNA without significantly changing DNA/RNA structure; it base pairs with Thymine/uracil with almost the same melting temperature (Tm). The introduction of 2-AP into both DNA and RNA oligonucleotide sequences in a site-specific manner is rather straightforward since it is relatively stable and available in phosphoramidite form for standard automated oligonucleotide synthesis. 2AP is a mildly fluorescent base. Its excitation wavelength is around 310 nm and it emission wavelength is around 370 nm. The quantum yield (QY) of free 2-AP-riboside at 25° C., pH 7.0 is 0.68, relative to quinine sulfate in 0.5 M $H_2SO_4$.

The fluorescent pteridine-based nucleoside analogues share some unique structural features. Their excitation wavelength is around 330-350 nm and their emission wavelength is around 430-440. 4-amino-6-methyl-pteridon (6MAP) is an analogue of adenine, and 6-Methylisoxanthopterin (6-MI) is that of guanine. 6-MI monomer has a QY of 0.70. For 6MAP, relative quantum yields are 0.39 as monomers and range from >0.01 to 0.11 in oligonucleotides.

Py-C is a fluorescent analog of cytosine. In hybridization state, py-dc has a QY of 0.07 in single-stranded and 0.02 in double-stranded. An ON fully substituted with py-C has the same melting temperature (Tm) as with (d)G. Py-C does not perturb the structure of the DNA helix in a substantial way and it is well tolerated by a number of DNA or RNA polymerises. Py-C's excitation wavelength is around 350 nm and its emission wavelength is around 460 nm. Py-C's excitation and emission are well to the red of the autofluorescence of biological fluorophores, which reduces background noise.

These fluorescent bases are well designed as structural analogs to the natural bases to minimize the perturbation of the formation of helix and normal interaction with enzymes. They exhibit much higher fluorescence quantum yields than the natural bases. Their fluorescence properties are very sensitive to the conformational change and binding situations, therefore are suitable as pseudo-intrinsic probes in nucleic acid molecules' characterization. Like in natural nucleosides, they attach to the oligonucleotide through a (deoxy)ribose linkage and, since they are available as phosphoramidites, they can be site-specifically incorporated into DNA using automated DNA synthesis.

Identification of additional fluorescent nucleotides suitable for practice of this invention can be accomplished with simple, rapid, and routine screening. The fluorescent bases in question are simply substituted into a nucleic acid molecule such that thus modified nucleic acid molecule obtains detectable fluorescence emission. In particular, an ON's natural base(s) is/are substituted by corresponding FBA(s) in their standard synthesis process, the fluorescence of the modified ON molecule is then measured. When the ON is hybridized to a complementary nucleic acid to form a hybrid duplex, the fluorescence level of the hybrid duplex is again determined. Those fluorescent base analogues that show measurable changes of its fluorescent properties, such as intensity, shift of spectra, lifetime and/or anisotropy, may be used in the direct excitation labeling of this invention for the general characterization. For those base analogues demonstrate energy transfer from normal bases, their fluorescence may be induced by the excitation of their adjacent normal bases in the range of 240-280 nm. These base analogues may be used in the indirect excitation labeling of this invention. Those base analogues that may form fluorescent excimers revealed by stepwise cross scanning may be used in the excimer labeling of this invention.

It should be noticed that the fluorescence intensity of the base analogues is sequence dependent on their neighboring bases, position in the sequence, temperature and pH of the matrix measured in. It is desirable to choose the fluorescence base analogues with more red-shifted excitation and emission wavelength and with higher QY. Those base analogues which give significant change of its fluorescence when so modified ON molecules are hybridized to a complementary nucleic acid sequence, bound to proteins or other biomolecules are better choice.

One of skill in the art will appreciate that the using of FBA modified nucleic acid in this invention can be optimized for particular applications. Such optimization can include varying the number of fluorescent base analogues in the nucleic acid molecule, varying the type, combination and position of the substituting base analogue(s), and varying the selection of nucleotides flanking the fluorescent base analogues. Determination of the optimal fluorescent base arrangement involves preparing the variants in question and screening them for changes in fluorescence activity on hybridization to a complementary nucleic acid sequence by using a spectrofluorometer. Those FBA arrangements that give the modified nucleic acid greater changes in fluorescence on hybridization are generally preferred.

Where the nucleic acid molecule is to be used in conjunction with a nucleic acid binding protein, the binding protein will be used in the assays instead of complimentary sequences described above. The assay conditions should also be modified from hybridization conditions to conditions that favor binding of the particular nucleic acid binding protein to a nucleic acid. Those base analogues that give the modified ON greater changes in fluorescence on protein binding are generally preferred.

2. The Use of Fluorescent Base Analogues as Intrinsic Probes

Three preferred embodiments are discussed in this invention. They are the use of fluorescent base analogue substitution in the direct excitation labeling scheme, in the indirect excitation labeling and in excimer emission labeling.

A) Direct Excitation Labeling

It was described above that fluorescent base analogues substantially retain the natural nucleotides' biological and chemical nature while generate measurable fluorescent signal, which is sensitive to the interaction with other molecules. The fluorescence of the base analogues is substantially quenched when it is incorporated into the nucleic acid sequence. The fluorescence may be recovered, or further quenched by the interaction with other molecules. Without being bound by a particular theory, it is believed that alteration of the normal stacking conformation or the hydrophobic/hydrophilic environment of the nucleic acid molecule at the location of the fluorescent base analogue reduces or increases the quenching effect thereby causing a change in fluorescence intensity. Thus, in some embodiments, this invention provides methods to characterize this general behavior and local environment of a nucleic acid molecule.

In one kind of embodiments, nucleic acid molecule is modified by substituting the normal base(s) by its fluorescence base analogue(s) into the corresponding position in the sequence. More preferably, the substitution is at the 5' terminus or 3' terminus. The modified nucleic acid will remain essentially the same physiologically until the object is specifically examined for the presence of the fluorescent base, e.g., by illuminating the object with an appropriate excitation light source within the range of excitation wavelength of those fluorescent bases. Such labeling provides a means of monitoring former undetectable natural nucleic acid molecules in physiological matrix.

An example of direct excitation labeling arrangement is illustrated as formula I:

```
5' GCATTAATTCGC 3'

→ Formula I

5'GC(2AP)TTAATTCGC 3'            (SEQ ID No. 1)
```

Although the position of substitution is determined by the normal base to be substituted, attention should be paid for the sequence dependent quenching and spectra shifting. It has been discovered that pteridine analogues are more quenched by purine bases. Thus, in some preferred embodiments the pteridine fluorescent base analogue(s) should not be positioned in adjacent to adenosine or guanosine. 2AP is particularly more quenched by adjacent guanine, therefore, in direct labeling, the candidate adenine should be chosen from those positions without adjacent guanine. Spectra shifting are also moderately dependent on the solvent, salt concentration, pH, and temperature of the system. The problem of quenching and spectra shifting necessitate preliminary test of the fluorescent base analogue in the target positions and conditions. For direct excitation labeling, quenching and shifting test should be done to identify the strongest quencher and the best detection wavelength in the interested matrix.

Quenching by natural base and shifting of spectra can be overcome by the use of indirect excitation scheme described at the part B of this section.

B) Indirect Excitation Labeling

It was discussed above that intramolecular energy transfer is generally available in nucleic acid sequence. It is this energy transfer that quenches the fluorescence activity of the fluorescent base analogues. This invention transforms this disadvantage into advantage by using indirect excitation via illuminating at natural bases' absorption wavelength.

Figure 3:
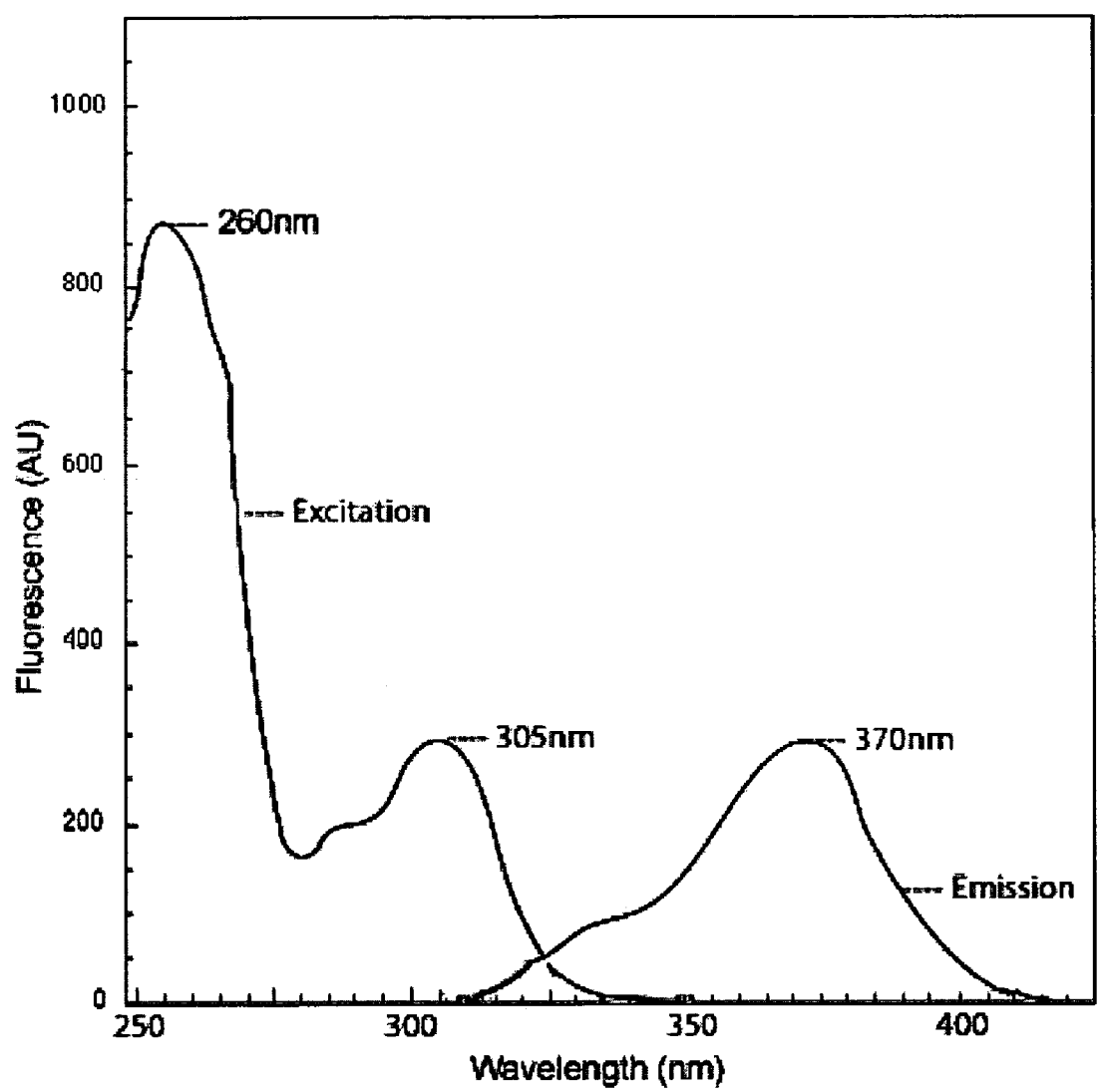
FIG. 3: Excitation spectrum and emission spectrum of 2-Aminopurine in Formula I. Excitation peak around 260 nm indicates intrasequence energy transfer for indirect excitation.

FIG. 3 demonstrates a general excitation phenomenon for fluorescent base analogue 2AP incorporated in an ON as Formula I, single-stranded.

```
5' GCATTAATTCGC 3'
→ Formula I

5'GC(2AP)TTAATTCGC 3'          (SEQ ID No. 1)
```

Fluorescence emission spectrum of the modified ON in aqueous medium gives a maximum around 370 nm. By monitoring this wavelength, excitation spectrum was determined. It shows that, in addition to the typical excitation maximum around 310 nm, there is a stronger excitation peak around 260 nm. This peak seats at the normal absorption range of natural bases, where 2AP monomer doesn't absorb.

Absorption spectra of individual bases are well known for those skilled in the arts. Normal bases' UV absorption spectra are substantially overlapped from 240 nm to 280 nm. It is well known that the average natural base absorption peaks around 260 nm. I found that FBA may generally be indirectly excited by the energy transfer from the neighboring normal bases illuminated around 240 nm-280 nm. The excitation at these wavelengths indirectly induces strong fluorescent activity of the selected fluorescent bases analogues in FIG. 2.

The term "indirect excitation" via normal bases, as used herein refers to a novel methods of fluorescence inducement by energy transfer via exciting adjacent normal base or bases in neighboring sequence instead of excite the fluorescent base analogue(s) directly. This scheme places fluorescent bases analogues into the nucleic acid sequence and test its fluorescent activity by indirect excitation via energy transfer from adjacent normal bases. Virtually any measurable energy transfer to the fluorescent base(s) is useful. However, the more efficient the energy transfers, the higher the fluorescent QY. Identifying the excitation wavelength with the best indirect induced fluorescent activities can be achieved by monitoring the fluorescent intensity at the emission wavelength of the fluorescent base analogue and scanning the fluorescence excitation spectrum from 240 nm to 280 nm of the studied nucleic acid containing the fluorescent base analogue in the target condition. The excitation wavelength gives a higher fluorescent intensity of the base analogue is preferred.

The fluorescent nucleic acid of this invention may contain multiple fluorescent base analogues of the same or different kinds. The indirect excitation method provides a way to simultaneously excite multiple different fluorescent bases in the nucleic acid sequence. Since the selected fluorescent base analogues generally accept energy transferred from normal bases, illumination at the overlapped normal base absorption wavelength may facilitate the simultaneous excitation of different kinds of the bases analogues present. It is well know to the skilled in the art that the most significant overlapping range of the normal bases' absorption is around 260 nm. Thus, excitation around 260 nm gives a fluorescent spectrum including the fluorescence peaks of all bases analogues in the nucleic acid molecule positioned by this indirect-excitation labeling scheme.

The simultaneous multiple labeling scheme transforms the undetectable normal nucleic acid into a sensitive probe of itself. If the position of the substituting fluorescent nucleotides are so selected such that they seat at the section that may character the conformational change or binding situation of the whole molecule, the profile of the fluorescent spectra resulted may characterize the dynamic conformation under the influence its environment. This is typically accomplished when the fluorescent base analogue(s) are positioned in representative sections within the nucleic acid sequence, such as the middle section plus both ending sections. A binding/conformation profile may be derived from the fluorescent spectra so generated by this method. Combined with other fluorescent measurement, such as anisotropy or fluorescent life-time, a comprehensive characterization of the nucleic acid molecule's interaction may be figured out.

The simultaneous detection of multiple heterogeneous fluorescent bases' fluorescence for the overall conformation/binding profile can be arranged by substituting fluorescent bases into the separate positions of the nucleic acid drug molecule. The position can be in the physical sections represent the overall conformation, or in the biological significant sections involved in dynamic interactions.

In the indirect excitation method, the excitation is from the simultaneous excitation of normal bases, instead of direct excitation one by one. Comparing with the direct excitation for multiple heterogeneous substitutions, which need to be done one by one at their individual excitation wavelength and monitor at their respective emission wavelength, it is much convenient by using indirect simultaneous excitation method disclosed here. By examine the emission spectrum, one may tell the situation of every fluorescent base analogues at its specific position, therefore, the spectrum gives a real time picture of the whole nucleic acid's conformation and structure under the interaction and influence of the matrix interested.

Although the averaged normal bases' excitation peaks at 260 nm, the best excitation wavelength should be tested in the matrix interested. Just as the direct excitation of the individual base, the fluorescent peaks by simultaneously excitation may be shifted or broadened. Caution should be taken to choose the excitation wavelength and identify the emission peaks. It is recommended to adjust the monitoring emission wavelength according to the new spectra to facilitate better sensitivity.

In the interaction within biological environment, nucleic acid molecule may be cleaved (hydrolyzed) by nucleases; certain base may be flipped out by specific enzymes. Fluorescent base analogues may also be replaced by DNA/RNA repair mechanism, which replace the non-natural fluorescent base by the normal base and liberalize the former quenched fluorescent bases in the stacking position of the nucleic acid molecule. The normal planar base stacking may be disrupted when the fluorescent oligonucleotide is bound by a protein (e.g., rec A protein, PI nuclease, HIV integrase, estrogen receptor, etc.). In the pharmacokinetic and pharmacodynamic study of nucleic acid drugs, direct labeling method has a problem of over counting and misreporting the presence of intact nucleic acid drugs by reflecting the presence the fluorescent base analogue itself, even if it has been cleaved out and lost its pharmaceutical activities.

By the indirect excitation method, fluorescent base's fluorescent activity is bound with its neighboring normal bases. Any disturbance of the normal stacking may be detected by the change of the nucleic acid molecules fluorescent properties. These disruptions reduce or eliminate the energy transferred resulting in reduction or elimination of their fluorescence activity induced by indirect excitation. If the nucleic acid molecule was degraded by enzyme and the fluorescent base analogue is cut, the excitation energy transferred from neighboring bases are cut off also. Therefore the degraded nucleic acid piece will not have the same fluorescent activity as the intact molecules. Hence, this labeling scheme also facilitates the quantitative pharmacokinetic and pharmacodynamic characterization of nucleic acid drugs.

By bounding fluorescent activity of the base analogue to the whole nucleic molecule, instead of let the fluorescent base signal the presence of itself, the indirect excitation labeling scheme reveals the integrality and activity of the whole nucleic acid molecule. This method makes fluorescent assay a more general reporting technique for nucleic acid molecules under the interactions with its environment. Its sensitivity allows the detection both the interaction with small molecule, such as hydration interaction, as well as the binding events with macromolecule resulting complex formation.

Indirect excitation promotes the normal base into its excited state. This may affect the biological activity of the nucleic acid molecule and result false reporting of their natural interaction. In this labeling scheme, the excitation exposure must be minimized. It is recommended to use pulse excitation instead of continue excitation.

C) Excimer Emission Labeling

It is the unique configuration of nucleic acid molecules, such as the close proximity and precise stacking orientation, facilitates the non-resonance energy transfer and excitonic coupling at biological temperature. The normal stacking of bases put adjacent base in close proximity (Helix rise per base pair 2.9 Angstroms for A-DNA, 3.4 Angstroms for B-DNA) and similar orientation (helical twist per base pair 31° for A-DNA, 36° for B-DNA). Significant ground-state interaction between two adjacent bases may result in local transition dipole moments of the individual base units strongly coupled and new fluorescent emission produces. Therefore, it is reasoned that, in the nucleic acid sequence, excimer formation is generally available. Excimer fluorescence of base analogues may be facilitated by substituting identical base analogues into adjacent positions in the nucleic acid molecule. The fluorescent activity may improve significantly when several base dimers are present, therefore, more than two of the identical bases are substituted into adjacent positions may increase the fluorescent intensity of the recorded spectra.

To form a coupled dimer in parallel configuration has to distort a little bit of the RNA/DNA's normal stacking. The excimer is in the lower energy level than excited single base, because of the looser structure of dimer as a unit comparing with single bases. Therefore the excimer fluorescent emission is necessarily red-shifted. The longer wavelength emission by the excimer may further distinguish the signal from the automate fluorescence of the biological environment.

The red-shifted emission may originate from both statically excited dimer and dynamically formed excimers from excited adjacent bases through intersystem coupling. This coupling arises from the relaxation of the excited bases, thus, it may serves as a second pathway for the excited individual base with identical bases as neighbors. Therefore, direct excitation of multiple base analogues in the adjacent configuration may reveal excimer fluorescent emission. The use of excimer labing via the excimer fluorescent emission generated by either excitation of dimer or direct excitations of the individual bases are both in the scope of this invention. In nuclei acid molecules, excited complex formation is not restricted to identical bases or fluorescent base analogues. But this invention claims the usage of excimer formed from the arrangement of identical fluorescent base analogues.

Since excimer formation is facilitated by the stacking proximity and orientation, it is sensitive to the nucleic acid molecule's conformation and binding status. When nucleic acid is in stable binding, or in the binding causing a significant change of the ON's stacking conformation, the formation of the dimer will be less feasible. In addition, dimer's formation is more facilitated inside nucleic acid sequence. When the adjacent base analogues are cut off by nuclease, the free ending base analogue has more degree of freedom at their orientation, therefore, there will be less possibility to form coupled dimer. In these conditions, excimer fluorescence emissions are lower. This excimer emission labeling is another way to tie the fluorescent signal of base analogues into the intact free nucleic acid molecule. It may effectively expose the whole molecule's integrality and activity.

The excimer fluorescence may be located by routine fluorescent spectroscopy techniques. In general, scanning the fluorescent emission in the red-shift side of the emission wavelength of individual base analogues while stepwise illuminating the multiple adjacent fluorescent bases at the red-shift side of its excitation wavelength pinpoint the emission peak and the excitation wavelength of the eximer. This stepwise scanning of the excitation and emission wavelength is a little bit more tedious. Since intersystem coupling may occur from the excited single bases to form the eximers, excimer emission may become the ancillary fluorescent event of the direct excitation of the individual bases in adjacent positions. Scanning the emission at the red-shift side by direct excitation of the individual base analogues in adjacent positions can be used to locate the excimer's fluorescent emission wavelength. This direct excitation induced eximer emission may be very weak, so caution should be paid to locate it. Then, while monitoring the fluorescence at the excimer emission wavelength so located, scanning the red-side of the base analogue excitation wavelength may reveal the excitation wavelength of the coupled dimer.

An example of excimer labeling arrangement is illustrated as formula II:

5' GCATTAATTCGC 3'

→ Formula II

5'GCATT(2AP)(2AP)TTCGC 3'          (SEQ ID No. 2)

Figure 4:
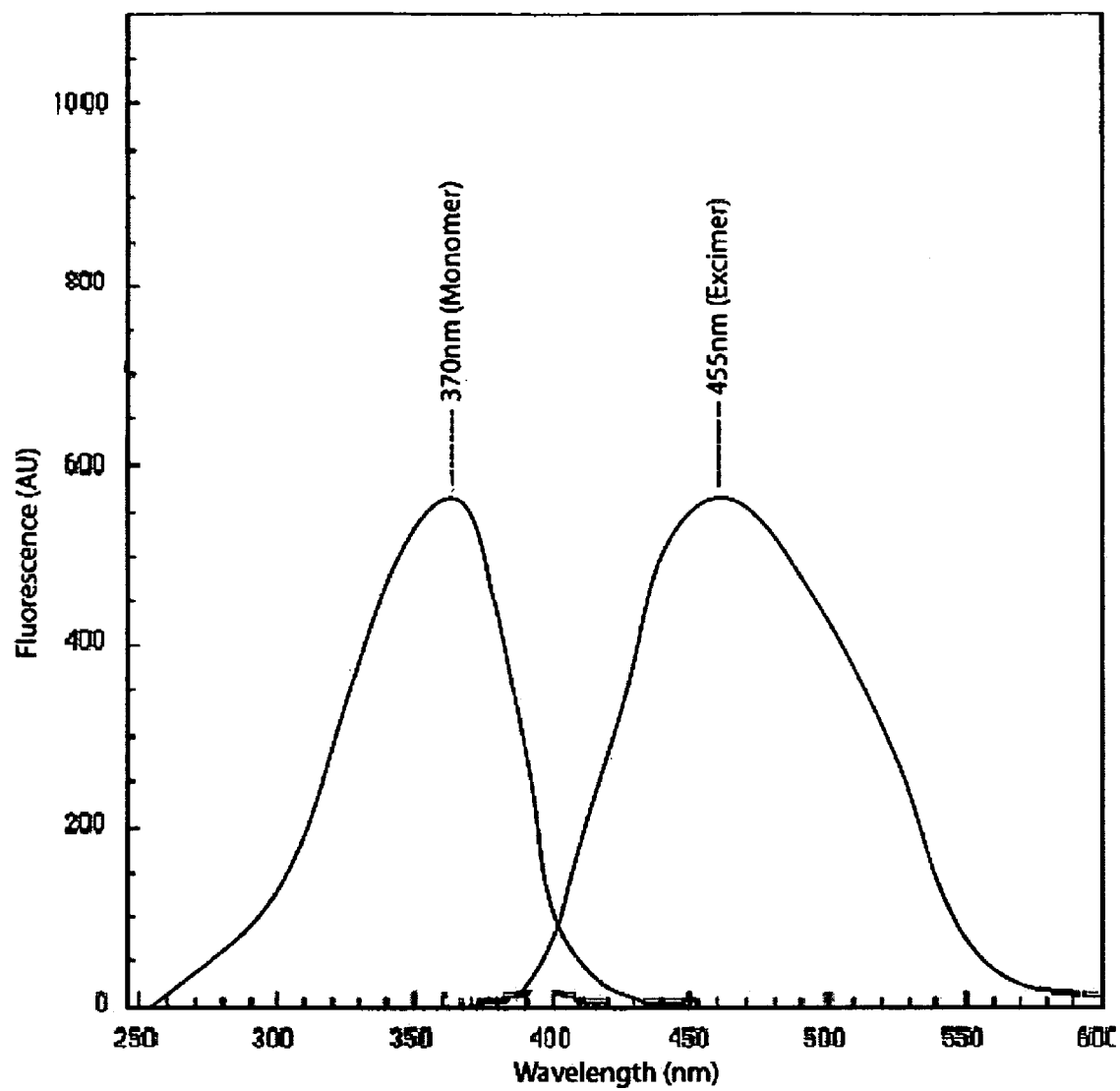
FIG. 4: 2AP excimer's fluorescence emission spectra of Formula II: emission peaks at the wavelength around 455 nm. The regular 2AP monomer's fluorescent emission spectrum is also included.

The excimer spectra of the Formula II is illustrated in FIG. 4.

For those of kill in the art, it is obvious that the above labeling schemes may be combined together for some applications. Caution should be taken for the interference of the different labeling schemes. It should be noticed that quencher is different with the inefficient donor. For the combined use of the direct general labeling and indirect excitation labeling, separate test should be conducted for the identification of the strong quencher and weak donor. Although for both tests, the monitored emission wavelength is the fluorescence wavelength of the base analogues, the excitation wavelength used is not the same. For quencher test, the excitation wavelength is that of the direct excitation of the fluorescent base analogue; for energy transfer donor test, the excitation wavelength has to be in the absorption range of the respective normal base.

Another example is the combined use of direct or indirect labeling and excimer labeling. One might think that multiple base analogues in adjacent positions might give stronger signal than single substituting by direct excitation. It is not true, however. Excimer emission may serve as another pathway for the excited individual bases analogues in adjacent positions; therefore, the fluorescence intensity at the typical individual base analogue emission might be lower than singly positioned ones. Judgment needs to be made for the combined labeling applications. Nevertheless, using the teaching in this invention in a way of combining the labeling schemes is in the scope of this invention.

In the above embodiments, species that can be so labeled include virtually any molecules contains nucleic acids. One of skill will appreciate that a substitution need not be produced by actual physical replacement of one or more natural nucleotides (bases) within a nucleic acid in vivo, but rather simply synthesize oligonucleotides with the interested sequence or subsequence de novo. The fluorescent base analogue labeled oligonucleotide sequence of this invention can be prepared by any of a wide variety of chemical and enzymatic methods. Chemical synthesis can be performed in solid phase or in solution. Generally, solid phase synthesis is preferred. Detailed descriptions of the procedures for solid phase synthesis of oligonucleotides by phosphite-triester, phosphotriester, and H-phosphonate chemistries are widely available. Alternatively, the substitution can be created by deleting one or more nucleotides in other so labeled sequence or subsequence, or by ligating (e.g., polymerizing) a sequence or subsequence with one or more nucleotides so labeled to form the complete desired nucleic acid molecule. Also, the label oligonucleotides of this invention can be prepared using enzymatic methods. This typically involves providing a template having a nucleotide sequence complementary to that of the desired label oligonucleotide. The label oligonucleotide is then produced by primer extension through polymerization of nucleotide triphosphate in solution using a nucleic acid polymerase (e.g., DNA or RNA polymerase). In this instance, the fluorescent oligonucleotide analogues are provided as nucleotide triphosphate for incorporation by the polymerase. Methods of enzymatically synthesizing nucleic acids are well known to those of skill in the art.

The entire properties associate with the fluorescence activity revealed by above labeling schemes may be used to characterize the nucleic acid molecule so tested. Excitation and emission wavelength may shift with the excited molecules' electron state, which may reveal the configuration of the molecules. Excitation absorbance and fluorescent intensity may associate with the binding state, conformational change or amount of the molecule tested. Lifetime may reveal the nature of intermolecular interaction and anisotropy may disclose the mobility of the molecule. For well designed labeling methods in this invention, the signal of fluorescent base may be tied with the behavior of the whole nucleic acid molecule, and therefore, the measurement of the fluorescence signal of the base analogue or its excimer may serve as a reliable detection of the properties of the whole nucleic acid molecule so labeled.

Means of detecting the fluorescence signals produced by the base analogue labeling scheme of this invention are well known to those of skill in the art. Fluorescence measurements can be carried out in any research grade fluorescence spectrometer. Typically detection is the same as that for any traditional fluorescent probes. Such detection involves exposing the fluorescent moiety (i.e., the fluorescent oligonucleotide) in the interested medium to an excitation illumination at the suitable wavelength of labeling schemes. The light is re-emitted at the emission wavelength of the fluorescent base analogues or its excimer. Detecting devices for fluorescent probe are commercially available and include, but are not limited to, fluorescence spectrophotometers, fluorometers, fluorescence microscopes, flow cytometers, fluorescence plate readers, and the like. The uses of such fluorescence detection devices are well known to those of skill in the art.

Figure 2:
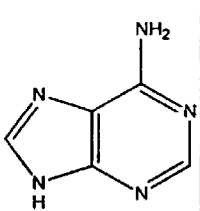
FIG. 2: Preferred nucleoside and its fluorescent analogues with their respective excitation and emission maximum.
Figure 2:
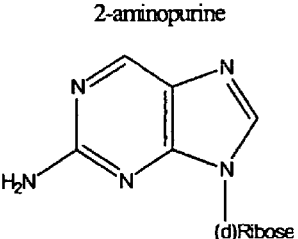
Figure 2:
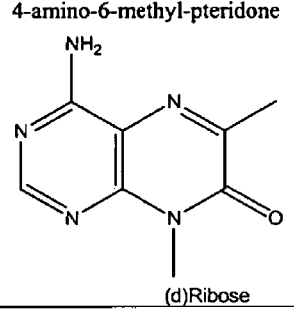
Figure 2:
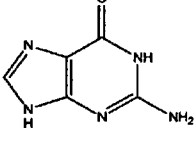
Figure 2:
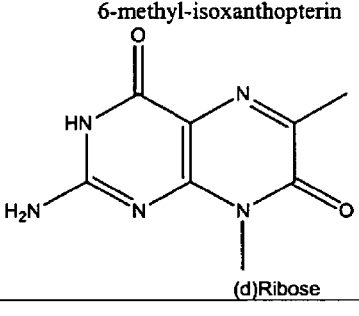
Figure 2:
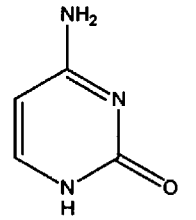
Figure 2:
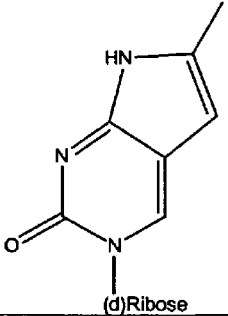

The use of small volume cells is convenient for minimization of sample usage; FIG. 2 provides guidance for placement of the excitation and emission monochrometers for the preferred base analogues. Low volume measurements can be made using an "H" style cuvette with excitation over the long (1 cm) path and emission through the short (2 mm path). 3 mm times 3 mm square cuvettes with a brass adapter have been successfully used. Fluorescence values for a specific substitution are usually normalized to the fluorescence of single-stranded DNA/RNA or double-stranded DNA containing the substitution(s) in vitro.

3. Fluorescence Detection Device for the Invention

The invention also provides a fluorescence spectrometer for the indirect excitation method. A spectrometer is a well-known optical system for the skilled of art. The invention of the device for indirect excitation labeling scheme is unique as that it utilizes fixed excitation and emission wavelength suitable for the application of the indirect excitation method for nucleic acids analysis.

In a fluorescence spectrometer, the sample to be analyzed is irradiated by excitation light, which causes the sample to emit fluorescence light at characteristic wavelengths. The fluorescence light is measured by a suitable detector. Typically, the wavelength of the excitation light is adjusted by selector, such as a diffraction grating or a filter. The fluorescence light emitted is usually analyzed by a second diffraction grating or by a filter. For performing a fluorescence measurement using indirect excitation method, the grating at the excitation side of the spectrometer is set to a fixed excitation wavelength in the range of 240 nm-280 nm and the wavelength spectrum of the fluorescence emission is recorded by the grating set at the emission wavelength of the incorporated fluorescent analogues. The emission spectra of multiple kinds of fluorescent base analogues can be recorded for a plurality of emission wavelengths if multiple filters set at the respective wavelength are used.

Figure 5:
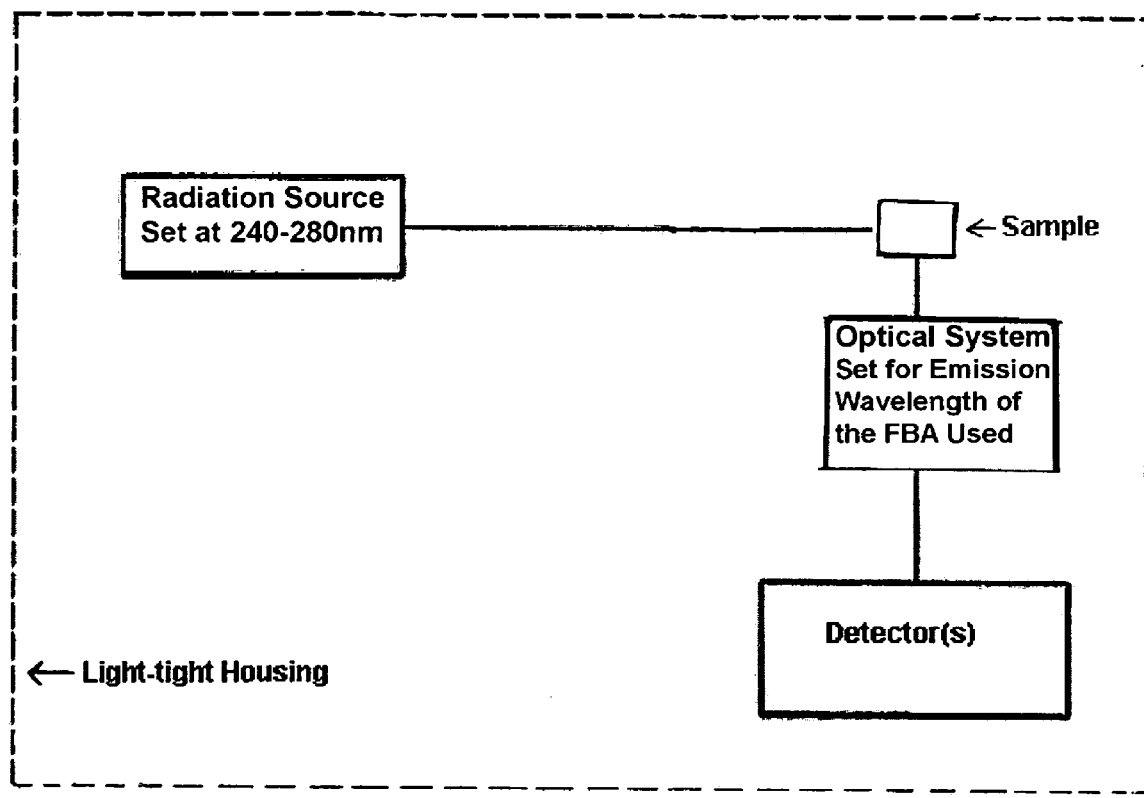
FIG. 5: A schematic chart of the fluorescent detection apparatus for the application of the invention method.

According to the invention, the device includes light-tight housing, a radiation source illuminates a fluorescent base analogue(s) incorporated nucleic acid sample at a wavelength in the range of 240 to 280 nm; an optical system that collects fluorescent light from the sample at the specific emission wavelength of the FBA(s) incorporated; and a detector system that senses the collected light and provides a fluorescence spectrum as a function of time. It may further include sample holder, controller coupled with the radiation source and the detector, a monochromator in the radiation source, an amplifier in the detector part, a computer, displayer or printer. (See FIG. 5)

The radiation source comprises a laser or flashlamp with the radiation wavelength in the range of 240 nm to 280 nm. In some embodiments, a lamp with a monochromator as a selector selective for a wavelength in the range of 240 nm to 280 nm is used.

The optical elements are arranged for imaging the spectrally separated radiation onto the detector. The optical elements may include parts for collecting the fluorescent light, selecting the emission wavelength of the FBA(s) incorporated sample and directing the selected wavelength to the detector. The wavelength selection may be achieved by using selectors. A typical selector is a monochromator consists of a diffraction grating (dispersing element), slits, and/or mirrors.

The detector set comprises photosensor(s), which can be CCD camera, photodiode or their combinations. The detector set may further include an amplifier.

It is a further object to provide simultaneous wavelength information in order to save time and costs, which would otherwise be caused by multiple analyses of the same sample. It is thus desirable to record the different wavelengths of the emission spectrum simultaneously, for example with an array of photosensitive detectors. In a preferred application, multiple selecting parts set for specific wavelength for respective FBA are used, which coupled with multiple detectors for simultaneous detection of the fluorescent activities of multiple kinds of fluorescent base analogues incorporated.

Figure 6:
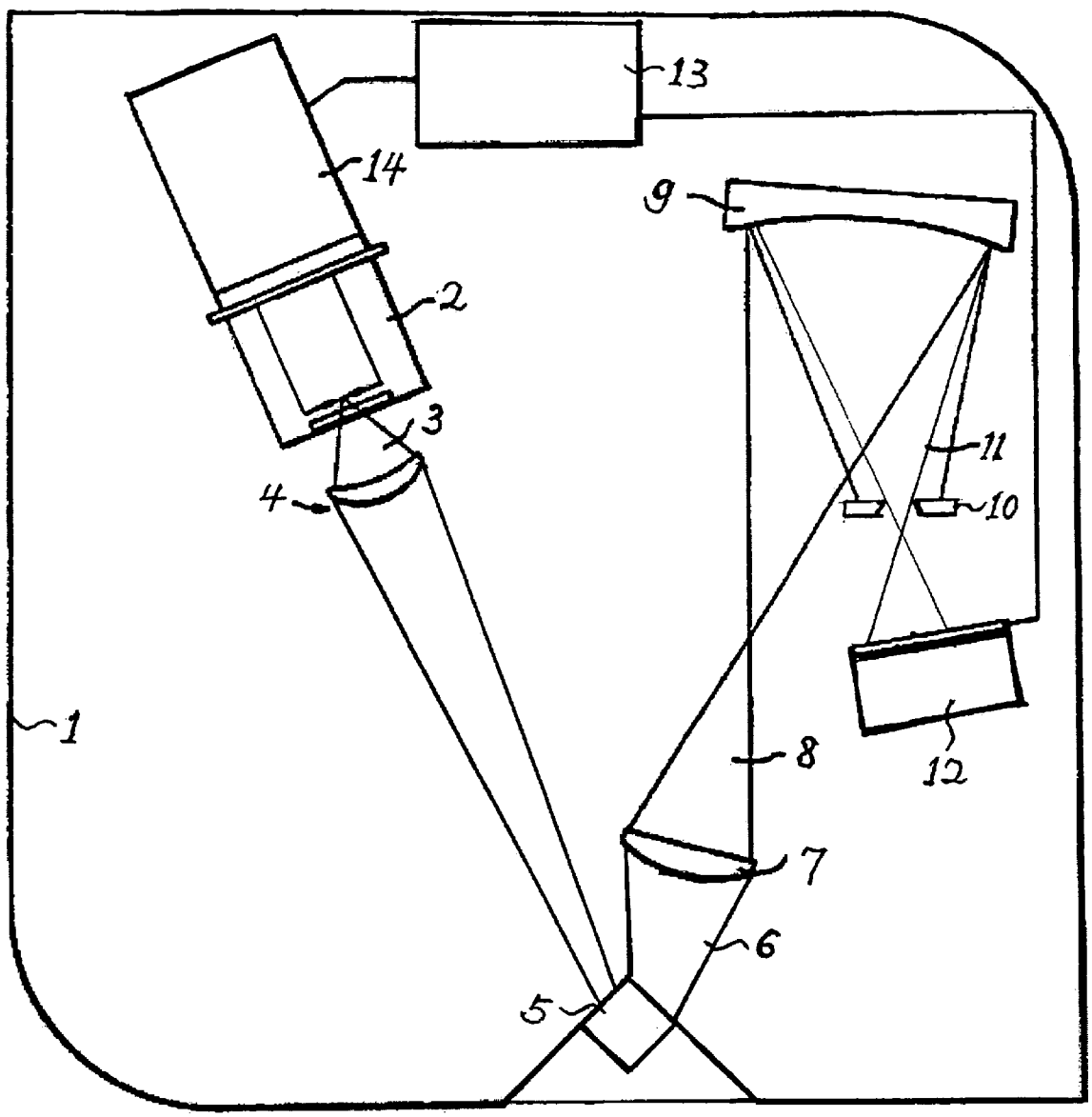
FIG. 6: A schematic diagram of a fluorescence apparatus according to an embodiment of the invention.

FIG. 6 is a schematic diagram of a fluorescence apparatus according to an embodiment of the invention. The components of the apparatus are arranged within a light-tight housing 1. The radiation for excitation is provided by a laser 2 arranged to emit radiation energy in the ultraviolet range of 240-280 nm. A first optical path portion extending between laser 2 and the sample in the holder 5, including lens 4. The lens is made of quartz so that light in the ultraviolet range is not absorbed.

The wavelength of the beam 3, i.e., the excitation wavelength, are set at the natural base's absorption wavelength is directed by the lens 4 to the sample holder 5 contains the sample substances to be analyzed. Typically, the sample holder is a quartz cuvette holding flow-through or stagnant nucleic acid solutions. The excitation light 3 excites the sample to emit fluorescence light. The fluorescence light 6 may received at any angle, but preferred to be collected at an angle of 90 degree.

Fluorescent light 6 propagates via a second optical path portion to the photodetector set 12. The second optical path portion includes optical elements of condenser lenses 7, wavelength selector grating 9 and slit plate 10. The beam 8 leaves the condenser 7 impinges on the diffraction grating 9 and passes through the slit 10. According to a practical example, the grating 9 and the slit plate 10 serves as a selector, which is selective for the emission wavelength of the specific fluorescent base analogue incorporated. The selected light 11 is directed to the detector 12.

For simultaneous detection of multiple FBAs' fluorescent activities, multiple selectors with gratings 9 set for the individual emission wavelength of the respective FBA are used, which coupled with multiple detector systems to ensure that the detector receives beams of the set wavelength.

When fluorescence emissions are detected, the light pulses of the laser 2 and the measuring time interval of the detector 12 are synchronized by a controller 13. Controller 13 is connected to the trigger or the shutter system 14 and to the detector 12. The detector 12 is controlled so the detector 12 reads out only after the laser 2 has emitted a light pulse. By using pulse light source, the photobleaching will be minimized by reducing the illuminating time.

It is evident that either the excitation wavelength or the emission wavelengths are fixed in this invention, so that the excitation light 3 entering the sample holder 5 is in a wavelength in the range of 240-280 nm and the emission light 6, which is selected at the specific wavelength of the fluorescent emission of the FBA incorporated, is incident on the photodetector 12.

It is understood that the invention is not limited to the above-described examples and that various modifications thereto are possible. For example, the radiation source may be a pulsed flashlamp or other source, which is capable of emitting pulses of radiation. A DC light source could also be used. Instead of a diffraction grating, an electrically or acoustically tunable filter or prism could be used as a diffraction element in the selector. The photosensitive elements for the detector may be, for example, avalanche photodiodes, charge coupled devices, diode arrays or intensified photodiode arrays (microchannel plates).

As can readily be appreciated, one advantage of the device is that it permits a real-time display of the behavior of the FBA modified nucleic acid molecules being examined. The result of a measurement according to the invention is twofold: 1) a chromatogram. i.e. a representation of the amount of sample substances as a function of time; 2) fluorescence spectra, i.e., representations of the intensity of fluorescence light as a function of time. The correlation between the amount of sample and the intensity of fluorescence can be established by standard calibration.

It is well known to those of skill in the art that, fluorescence measurements can be typically made in two ways: steady-state measurements and time-resolved measurements. Steady-state measurement is conducted with constant irradiation and observation. Due to the nanosecond time scale of the fluorescence of most fluorophores, when a sample is photoexcited, the steady-state condition, i.e. the equilibrium situation between excitation and decay for the system is reached almost immediately. Steady-state measurement is the most commonly used method. In contrast, time-resolved measurements involve the monitoring of a temporal dependence of a given fluorescence parameter, like emission intensity, wavelength or anisotropy. For the apparatus in this invention, the measurement can be taken either in steady-state or in the time-resolved technique. In the embodiment described above, the sample is exposed to a pulse of light that is shorter than the decay time of the sample and measurements are then made using a high-speed detection system capable of making discrete observations within a nanosecond time regime. The use of the above labeling schemes by either of these two measurements is in the scope of this invention.

Fluorescence lifetime detection is one of time-resolved measurements. Fluorescent photons are emitted at statistically random times, resulting in an exponentially decaying curve. The time it takes for 63% of the population to emit is referred to as the fluorescence lifetime. Another type of time-resolved measurement is Anisotropy. It involves the measurement of both horizontal and vertical components of fluorophore emission by using polarizers. Since rotation rates are slower for bigger molecules, this anisotropy measurement can indicate changes in the size of a molecule due to its unfolding or its binding to another molecule. If the anisotropy is calculated throughout the emission decay time, the resultant anisotropy lifetime can characterize the mobility of the detected molecules.

The complexity of the bio-system's fluorescent intensity decay is usually fit in a multiexponential model. The resulting lifetime data in phase and modulation is a characterization parameter for the molecule's behavior under the influence of the matrix. Time-resolved Fluorescence data were analyzed by standard deconvolution procedure using non-linear least square regression. The fluorescence intensity decay measured at the magic angle (54.7° from vertical) was fitted to a sum exponentials, $$K(t) = \sum_{i=1}^{N} a_i e^{-t/\tau_i}$$

where $a_i$ are the amplitudes of each component and $T_i$ are the corresponding fluorescence lifetimes. Decay curves were represented with the minimum number of components (N) required for best fit. For those exhibiting multi-exponential fluorescence decay behavior, the intensity-averaged fluorescence lifetime, $T_{int}$, was calculated according to:

$$\tau_{int} = \left[\sum_{i=1}^{N} a_i \tau_i^2\right] / \left[\sum a_i \tau_I\right]$$

The lifetime parameters recovered from the fit of the magic angle decay were applied to the anisotropy decay data collected for the same samples. Polarized intensity decays were fitted using the following expressions:

$I_{//}(t) = \frac{1}{3}[1+2r(t)]K(t)$ $I_{+}(t) = \frac{1}{3}[1-r(t)]K(t)$ where $I_{//}(t)$ and $I_{+}(t)$ are the intensity decays measured with the emission polarizer parallel or perpendicular to the excitation polarization, respectively, and $r(t)$ is the time-dependent fluorescence anisotropy. The latter was represented as a sum of exponential decays:

$$r(t) = \sum_{k=1}^{M} \beta_k e^{-t/\phi_k}$$

where $B_k$ is the limiting anisotropy of component k, $\phi_k$ is the corresponding rotational correlation time and M is the number of components. $I_{//}(t)$ and $I_{+}(t)$ were simultaneously fitted by adjusting the values of $B_k$ and $\phi_k$ while keeping the parameters in K(t) fixed at the values recovered from the analysis of the corresponding magic angle decay. The limiting anisotropy at time zero, r(0), was obtained by summing the individual $B_i$ values.

Time-resolved fluorescent detection may also be used in microscopy. Fluorescence lifetime imaging microscopy (FLIM) is a technology of the measurement of the fluorescence decay time at each point in a two-dimensional image. It is particularly useful for investigation of the real-time imaging of so labeled DNA/RNA in living cell. The analysis of the resulting curve can be easily done by using a computer with suitable software coupled with the detector.

Time-resolved fluorescent spectroscopy investigation may reveal dynamic processes undetectable by steady state measurement. Even if the fluorescence intensity is the same, the distinct lifetime may reveal different interaction of the molecule. The biological relevance of fluorescent lifetime is the distinguishing of different binding or interaction mechanism. Instead of showing the fluorescent probe's own lifetime decay, the labeling scheme of this invention makes the base analogue to be intrinsic probe to show the whole nucleic acid molecule's activity.

Figure 7:
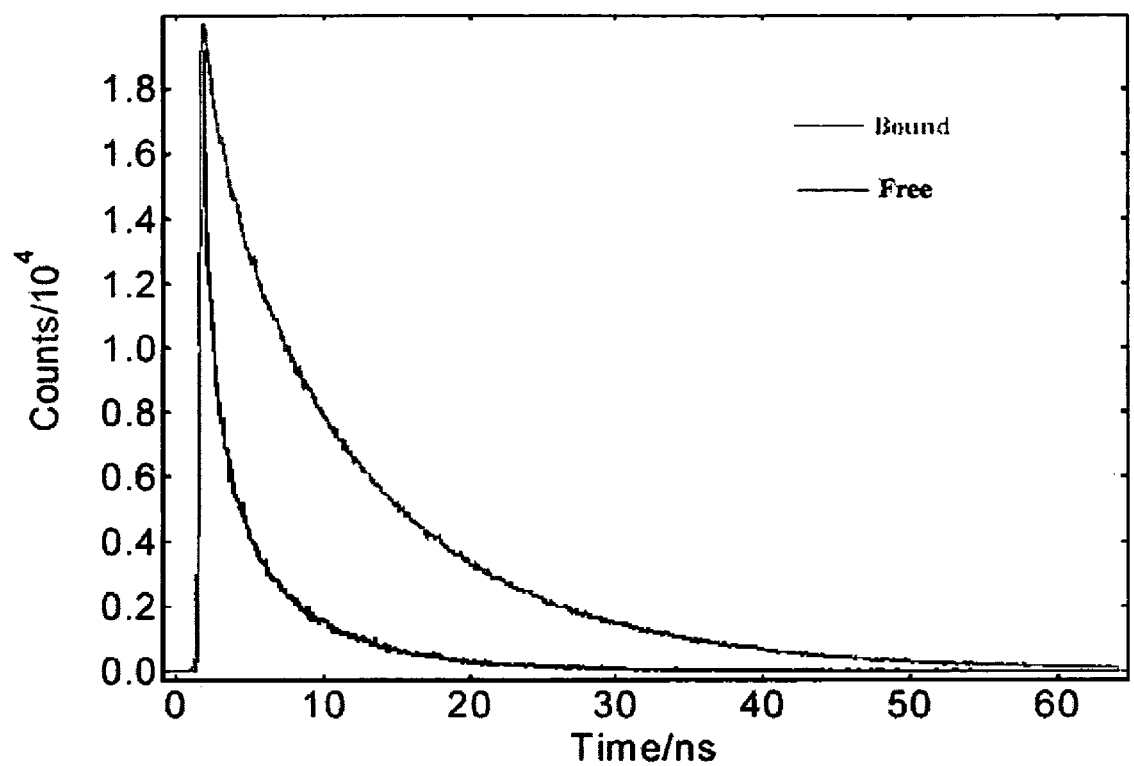
FIG. 7: The fluorescent lifetime decay a 2AP modified ON (Formula I). Black curve: ON in relatively free environment. Gray curve: ON in dynamic binding equilibrium with a nucleic acid binding protein.
Figure 8:
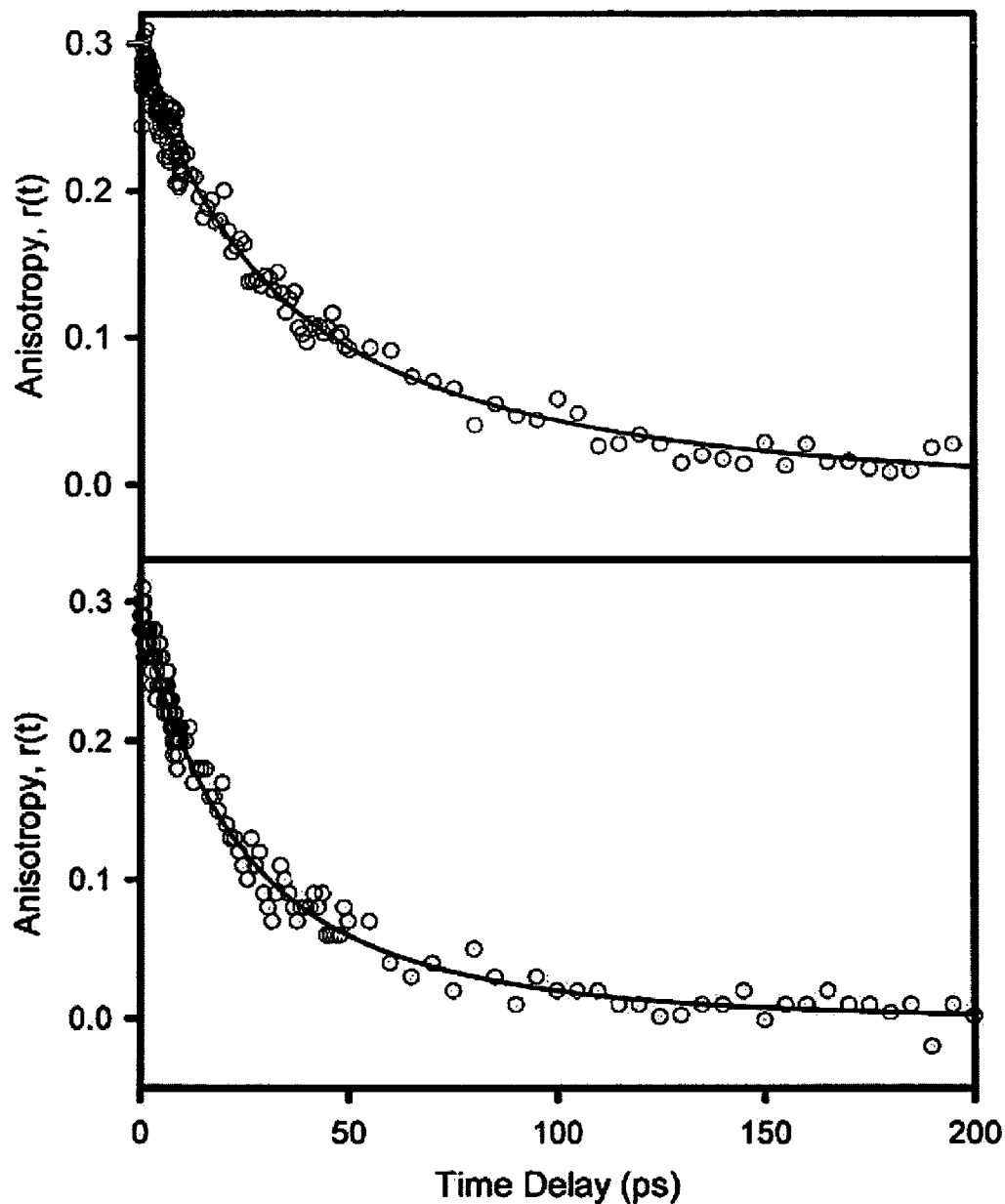
FIG. 8: Anisotropy lifetime curve of ON Formula I. Upper chart: anisotropy for the ON under a stable binding situation with a nucleic acid binding protein; lower chart: the ON in aqueous medium alone.

FIG. 7 demonstrates the fluorescent lifetime decay a 2AP modified ON (Formula I) under two interaction mechanisms with the same steady state intensity. Black curve with shorter lifetime is the fluorescent base analogues in relatively free environment. Gray curve is the base analogues in dynamic binding equilibrium with a nucleic acid binding protein. Substantially longer lifetime indicates an interaction with stabilizing effect of the excited state. Similarly, anisotropy lifetime curve as shown as FIG. 8 for the same ON sample indicates a substantial increase of the anisotropy for the ON under a stable binding situation with a nucleic acid binding protein, comparing with the ON in aqueous medium alone.

5. Enhancement of Reliable Detection.

By definition, a base analog is not an exact replacement for the biological corresponding base that it replaces. This presents a problem in the simulation of the true biological system. For example, a substitution that alters an energetically important protein-DNA/RNA contact is likely to lead to a false reporting signal of the true interaction. In practice of this invention, caution must be paid to how severe the selected fluorescent analog may influence the native behavior of the nucleic acid molecule. That the analyses can be less than straightforward is further illustrated by the fact that the absolute quantum yields (and precise mechanism of quenching) of fluorescent base analogs is sequence dependent. This dictates that the approach must be position specific.

Temperature is a variable, which should be considered carefully. Measurements in vitro are most readily carried out at 25° C., where enzymes are stable for extended periods. Measurements in vivo can be carried out at 37° C., but with less sensitivity.

For fluorescent probes with excitation and emission maxima far from that of the protein's, wavelength slits can be set fairly large (>5 nm). For measurements with 2AP, care should be taken to minimize fluorescence from protein's tryptophan groups. This can be achieved by setting excitation and emission monochrometers 5-10 nm to the red of the maximum shown in FIG. 2 (but with some loss in signal intensity). In any of these cases, fluorescence background from proteins should be subtracted (zeroed) by using parallel experiments running on nucleic acid molecules without 2AP.

In the case of substantial overlapping of the fluorescence emission spectrum with the autofluorescence spectra of the biological matrix, excimer emission method may be used to red-shift the detection spectrum.

In some embodiment that the fluorescence of the FBA modified nucleic acids can be transferred to the red direction through a second and even a third fluorophore. In this kind of embodiment, a second fluorophore is provided that has an absorption wavelength at or about the emission wavelength of the fluorescent base analogue. When a fluorescent base analogue is excited, the energy it releases is absorbed (e.g., through resonance energy transfer) by the second or third fluorophore, which then fluoresces at its characteristic wavelength. This approach is particularly convenient where it is desired to shift the signal to a wavelength different than the characteristic fluorescence wavelength of the fluorescent nucleotide analogue. Although this kind of resonance energy transfer systems is well known to those of skill in the art, the attachment of the bulky second and third fluorophores may substantially alter the chemical and biological behavior of the nucleic acid molecule, thus it is less preferred. Nevertheless, this kind of embodiments with indirectly detection of the fluorescent base analogues so labeled via other fluoreophore(s) is in the scope of this invention.

6. The Kit for the Application of this Invention

This invention also provides an application kit. The kit comprises a set of ON incorporating the fluorescent base analogues for quantitatively determination of the interacting effects on DNA/RNA molecules due to chemical interaction, biological activity or radiation influences. The kit may also be used for nucleic acid drug's kinetic simulation and nucleic acid drug's dosage determination.

The kit includes a set of fluorescent base incorporated ON with different permutation of the FBA on the critical positions of an ON. The kit utilizes the simultaneous indirect excitation method of this invention by place different FBA at different parts of a nucleic acid molecule for simultaneous excitation and detection. It may also come with suitable buffers for the stability and viability of the oligomers, such as, but not limited to, standard buffer for RNA (1 mM cacodylic acid, pH 6.5, 25 mM NaCl) or standard buffer for DNA (10 mM sodium phosphate (Na-Pi), pH 7.0).

An example of using the kit in enzyme kinetic study of DBA/RNA nuclease is give at following section. Data provided herein are only for illustration.

7. Application Examples

The following examples using one formula in the kit by indirect excitation is offered to illustrate, but not to limit the claimed invention.

A) Enzyme Kinetics

A double-strand oligodeoxynucleotides as Formula III with the sequence of SEQ ID No. 3, which is provided in one set of the embodiment of the kit:

```
5'GCATTAATTCGC 3'
  ||||||||||||
3'CGTAATTAAGCG 5'
```

→ Formula III

```
5'(6MI)CATT(2AP)ATTCG(Py)3'   (SEQ ID No. 3)
    |  ||||  |  ||||  |
3'  C  GTAA  T  AAGC  G 5'
```

Where 6MI represents 6-methyl-isoxanthopterin, a guanine analog, 2AP represents 2-aminopurine, an adenine analog, and Py represents pyrrolo-d(C), a cytosine analog. Concentration of the ON is determined by measuring their absorption at 260 nm for normal bases in the oligodeoxynucleotide without counting FBA (6MI, 2AP, Py) as a base.

FBA containing ON of Formula III is prepared as 0.1 uM solution by using the 1× buffer (1× concentrations=50 mM Tris-acetate, pH 7.5, 50 mM Na-acetate, 10 mM Mg-acetate, 5 mM DTT) provided in the kit. An aliquot of 5'- or 3'-nuclease solution is introduced into the ON solution and measure the fluorescence as a function of time, for 30 minutes. The spectrophotometer is set at anti-bleach mode to keep the shutter closed between measurements to minimize photobleaching. The data are collected in time intervals of 10 seconds by pulse excitation. Fluorescence intensity as a function of time was plotted.

Figure 9:
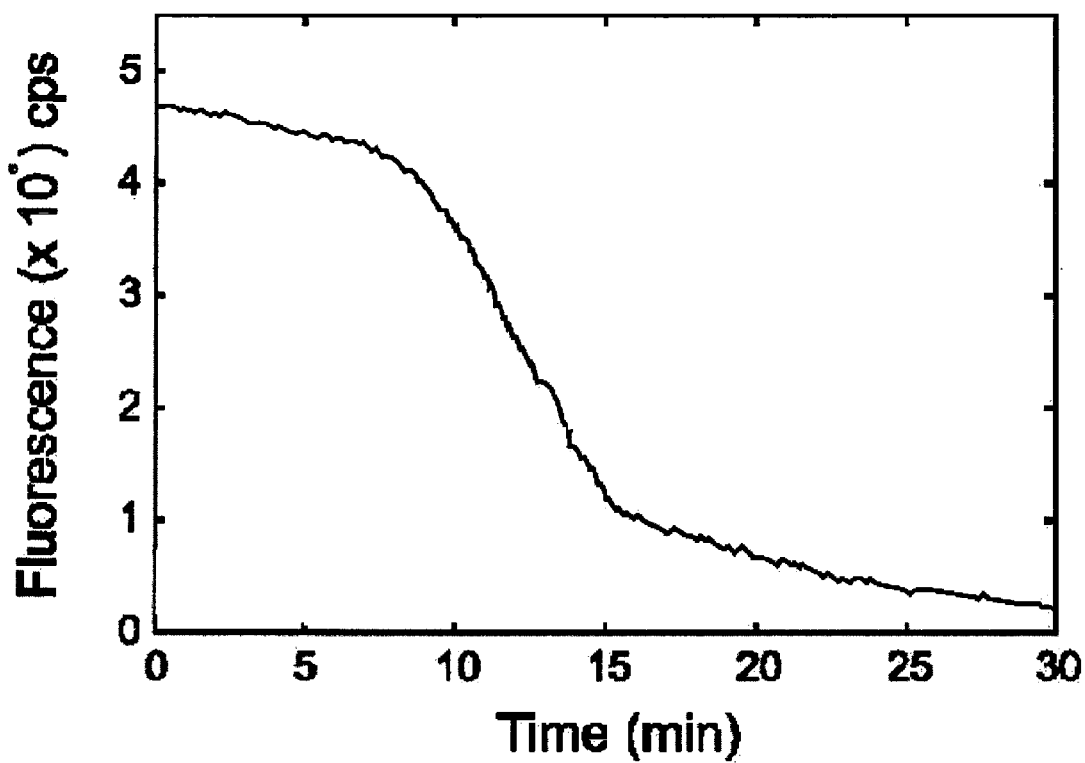
FIG. 9: Fluorescence enzyme kinetic assay for nuclease activity of Formula III. Generated by the indirect excitation measurement of fluorescent intensity of 2AP, ie. fluorescence intensity is measured at 370 nm by excitation at 260 mm.

FIG. 9 is generated by the indirect excitation measurement of fluorescent intensity of 2AP only, ie. fluorescence intensity is measured at 370 nm by excitation at 260 nm. The decrease of fluorescent intensity is due to the cleavage of the 2AP from the ON molecules. It is evident in FIG. 9 that free 2AP cleaved by nucleases lose its fluorescent activity by cutting off the energy transfer from the neighboring natural bases. The typical sigmoidal shape of the fluorescent intensity curve demonstrates the real-time activity of the enzyme tested. The final phase tailing to plateau is due to the level off of the substrate concentration dependent rate of the enzyme activity.

If the apparatus of this invention in the multiple detection embodiment is used, three curves as functions of time will be simultaneously produced. Combine the three curves, one may tell if the nuclease is 5' nuclease, endonuclease or 3' nuclease. The efficiency of the nuclease may also be determined.

B) A Simple Pharmacokinetic and Pharmacodynamic Investigation:

A single stranded DNA oligonucleotide with the SEQ No. 1 as Formula I:

5' GCATTAATTCGC 3'

→ Formula I

5'GC(2AP)TTAATTCGC 3'          (SEQ ID No. 1)

100 nM, 50 nM, and 25 nM of the above ON are introduced into 1 ml blood serum. Their fluorescence intensity is monitored by the indirect excitation method described above with excitation at 260 nm.

Figure 10:
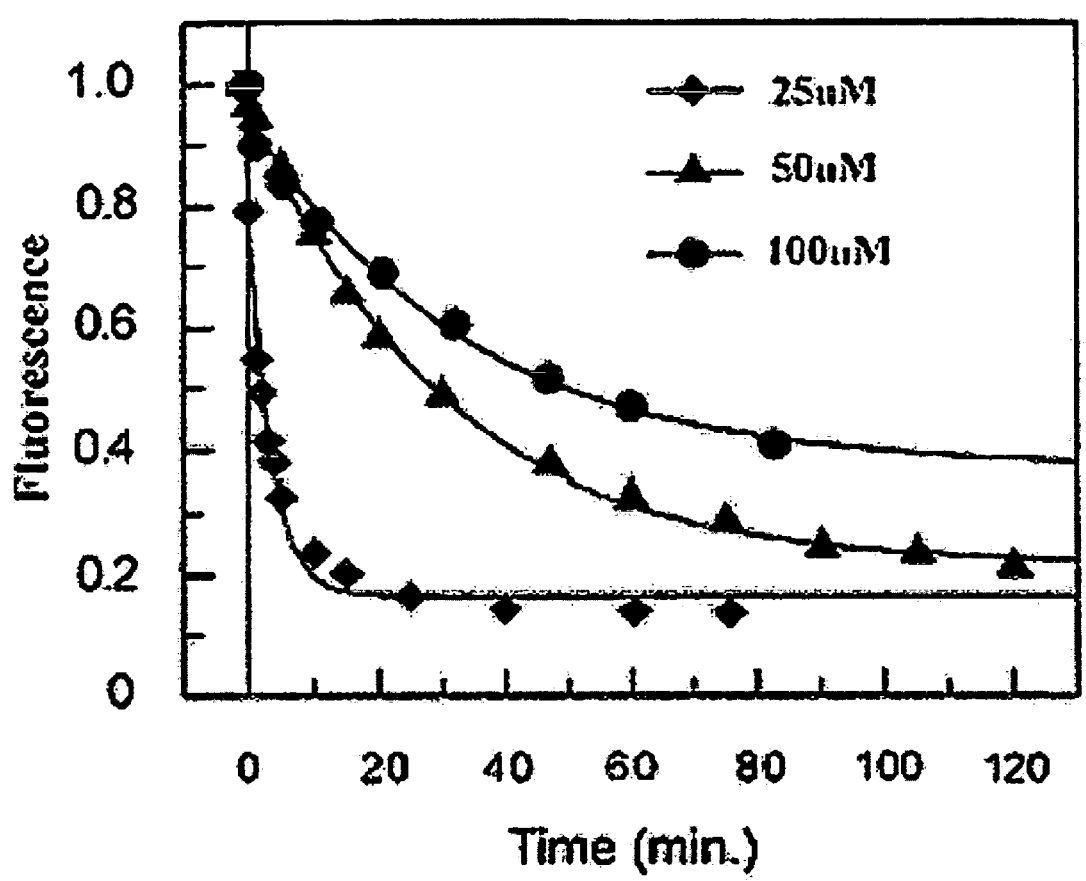
FIG. 10: PK/PD study of Formula I. The fluorescence intensity is monitored by the indirect excitation method with excitation at 260 nm and fluorescence emission measured at 370 nm.

The result is shown as FIG. 10. Data is collected along the time range of 2 hours by following the decrease in fluorescence at 370 nm. The time course of the decrease in 2AP fluorescence is attributed to the bioavailability depletion resulting from the degradation by enzyme, binding with protein or other biomolecules. Notice the substantially shorter halftime for the 25 nm dose and the substantially longer halftime for the 100 nm dose. It indicates a saturatable kinetics for ON depletion. If the ON concentration was calibrated for the fluorescent intensity in this media, the time course of free ON concentration may be constructed, which may facilitate further PK/PD modeling to direct the nucleic acid drug's delivery system design or dosage determination.

For a convenient fluorescence assay for kinetic study, a fluorescence spectrophotometer should be equipped with a stirrer and programmable to measure fluorescence as a function of time. In the above samples, all excitation spectra should be corrected by the excitation correction file included in the instrument software for lamp fluctuations. All emission spectra should be corrected for Raman signals of buffer blanks.

The application of this invention isn't limit to these examples. As stated above, in this invention fluorescence detection methods include, fluorometers, fluorescence microscopes, flow cytometers, fluorescence plate readers, and the like. Monitored fluorescence properties may include wavelength, absorbance, intensity, lifetime, etc. Matrix or medium, in which the invention is practiced, may includes, in vitro media, culture cell, tissue sample, circulating blood system, or in situ living tissues.

It is understood that the example and data described herein are for illustrative purposes only and that various modifications or changes of the embodiments for particular application will be suggestive to persons skilled in the art and are to be included within the purview of this patent application and scope of the appended claims.

In summary, this invention provides methods, apparatus and kits for the qualitative and quantitative characterization of nucleic acid molecules' structure and activity in vitro and in vivo by detecting the fluorescent activities of the FBA incorporated. The methods generally place one or more fluorescent base analogue into a nucleic acid molecule (e.g., an oligonucleotide) to replace the corresponding normal base(s). Without binding to any theory, the invented methods arrange fluorescent base analogues as intrinsic fluorescent probes by using direct excitation, indirect excitation, and excimer emission labeling schemes described above. One of skill in the art will appreciate that the methods of this invention can be used in a wide variety of contexts. These usages of the selected base analogues facilitate a comprehensive characterization of nucleic acid molecules.

A large number of fluorescent base analogues are suitable for use in the methods and compositions of this invention. Fluorescent base analogues include, but are not limited to the fluorescent bases analogues described in FIG. 1, their derivative and the like. In a particularly preferred embodiment, the fluorescent base analogues are those described in FIG. 2. One of skill in the art will appreciate that other fluorescent base analogues can be used in this invention.

All publications, patents, and patent applications cited are hereby incorporated by reference for all purposes.

What is claimed is:

1. A method of detecting the structures and interactions of a nucleic acid molecule, comprising:
   placing in said nucleic acid molecule or substituting corresponding nucleotide(s) of said nucleic acid molecule with one or multiple fluorescent nucleotide analogue(s);
   introducing so modified nucleic acid molecule into a target matrix or medium so as to subject the nucleic acid molecule to interactions with components in the matrix or medium; and
   detecting the structures and activities of said nucleic acid molecule by measuring fluorescence properties of the fluorescent base analogue(s) in said nucleic acid molecule at the fluorescent base analogue's respective emission wavelength by indirect excitation of nearby natural bases of said nucleic acid molecule at a wavelength in the range of 240 nm to 280 nm, in which the fluorescent base analogue is 2-aminopurine, and the emission wavelength is in the range of 350 nm to 380 nm.

2. A method of detecting the structures and interactions of a nucleic acid molecule, comprising:
   placing in said nucleic acid molecule or substituting corresponding nucleotide(s) of said nucleic acid molecule with one or multiple fluorescent nucleotide analogue(s);
   introducing so modified nucleic acid molecule into a target matrix or medium so as to subject the nucleic acid molecule to interactions with components in the matrix or medium; and
   detecting the structures and activities of said nucleic acid molecule by measuring fluorescence properties of the fluorescent base analogue(s) in said nucleic acid molecule at the fluorescent base analogue's respective emission wavelength by indirect excitation of nearby natural bases of said nucleic acid molecule at a wavelength in the range of 240 nm to 280 nm,
   in which the fluorescent base analogue is 4-amino-6-methyl-pteridone, and the emission wavelength is in the range of 410 nm to 450 nm.

3. A method of detecting the structures and interactions of a nucleic acid molecule, comprising:
   placing in said nucleic acid molecule or substituting corresponding nucleotide(s) of said nucleic acid molecule with one or multiple fluorescent nucleotide analogue(s);
   introducing so modified nucleic acid molecule into a target matrix or medium so as to subject the nucleic acid molecule to interactions with components in the matrix or medium; and
   detecting the structures and activities of said nucleic acid molecule by measuring fluorescence properties of the fluorescent base analogue(s) in said nucleic acid molecule at the fluorescent base analogue's respective emission wavelength by indirect excitation of nearby natural bases of said nucleic acid molecule at a wavelength in the range of 240 nm to 280 nm,
   in which the fluorescent base analogue is 6-methyl-isoxanthopterin, and the emission wavelength is in the range of 410 nm to 450 nm.

4. A method of detecting the structures and interactions of a nucleic acid molecule, comprising:
   placing in said nucleic acid molecule or substituting corresponding nucleotide(s) of said nucleic acid molecule with one or multiple fluorescent nucleotide analogue(s);
   introducing so modified nucleic acid molecule into a target matrix or medium so as to subject the nucleic acid molecule to interactions with components in the matrix or medium; and
   detecting the structures and activities of said nucleic acid molecule by measuring fluorescence properties of the fluorescent base analogue(s) in said nucleic acid molecule at the fluorescent base analogue's respective emission wavelength by indirect excitation of nearby natural bases of said nucleic acid molecule at a wavelength in the range of 240 nm to 280 nm,
   in which the fluorescent base analogue is pyrrolo-(d)C, and the emission wavelength is in the range of 440 nm to 480 nm.

5. A method of detecting the structures and interactions of a nucleic acid molecule, comprising:
   placing in said nucleic acid molecule or substituting corresponding nucleotide(s) of said nucleic acid molecule with one or multiple fluorescent nucleotide analogue(s);
   introducing so modified nucleic acid molecule into a target matrix or medium so as to subject the nucleic acid molecule to interactions with components in the matrix or medium; and
   detecting the structures and activities of said nucleic acid molecule by measuring fluorescence properties of the fluorescent base analogue(s) in said nucleic acid molecule at the fluorescent base analogue's respective emission wavelength by indirect excitation of nearby natural bases of said nucleic acid molecule at a wavelength in the range of 240 nm to 280 nm,
   wherein the multiple fluorescent nucleotide analogues incorporated comprises 2-aminopurine, 6-methyl-isoxanthopterin, and pyrrolo-(d)C; and
   wherein detecting the structures and activities of said nucleic acid molecule by simultaneously measuring fluorescence properties of 2-aminopurine, 6-methyl-isoxanthopterin, and pyrrolo-(d)C in said nucleic acid molecule at 2-aminopurine's emission wavelength around 370 nm, at 6-methyl-isoxanthopterin's emission wavelength around 430 nm and at pyrrolo-(d)C's emission wavelength around 460 nm.

6. A kit for the method of claim 5 comprising at least one piece of oligonucleotide incorporating three different fluorescent base analogues at three specific positions selected from the group of positions consisting of:
   1) 2-aminopurine at the 5' end portion, 6-methyl-isoxanthopterin at the middle portion, and pyrrolo-(d)C at the 3' end portion of the oligonucleotide;
   2) 2-aminopurine at the 3' end portion, 6-methyl-isoxanthopterin at the 5' end portion, and pyrrolo-(d)C at the middle portion of the oligonucleotide;
   3) 2-aminopurine at the middle portion, 6-methyl-isoxanthopterin at the 3' end portion, and pyrrolo-(d)C at the 5' end portion of the oligonucleotide;
   4) 2-aminopurine at the 5' end portion, 6-methyl -isoxanthopterin at the 3' end portion and pyrrolo-(d)C at the middle portion of the oligonucleotide;
   5) 2-aminopurine at the 3' end portion, 6-methyl -isoxanthopterin at the middle portion and pyrrolo-(d)C at the 5' end portion of the oligonucleotide; and
   6) 2-aminopurine at the middle portion, 6-methyl-isoxanthopterin at the 5' end portion and pyrrolo-(d)C at the 3' end portion of the oligonucleotide.

7. The kit in claim 6, wherein the fluorescent base analogue incorporated oligonucleotides are double strand.

8. The kit in claim 6, further includes a suitable buffer for the stability and viability of the oligonucleotides.

* * * * *

SEQUENCE LISTING

```
<160> NUMBER OF SEQ ID NOS: 3

<210> SEQ ID NO 1
<211> LENGTH: 12
<212> TYPE: DNA/RNA
<213> ORGANISM: Artificial
<220> FEATURE:
<223> OTHER INFORMATION: Short artificial sequence for illustration
<220> FEATURE:
<221> NAME/KEY: misc_feature
<222> LOCATION: (3)..(3)
<223> OTHER INFORMATION: 2AP

<400> SEQUENCE: 1
gcnttaattc gc                                                           12

<210> SEQ ID NO 2
<211> LENGTH: 12
<212> TYPE: DNA/RNA
<213> ORGANISM: Artificial
<220> FEATURE:
<223> OTHER INFORMATION: Short artificial sequence for illustration
<220> FEATURE:
<221> NAME/KEY: misc_feature
<222> LOCATION: (6)..(7)
<223> OTHER INFORMATION: n at position of 6 and 7 are the adenine's
      fluorescent analogs 2-aminopurine (2AP).

<400> SEQUENCE: 2
gcattnnttc gc                                                           12

<210> SEQ ID NO 3
<211> LENGTH: 12
<212> TYPE: DNA/RNA
<213> ORGANISM: Artificial
<220> FEATURE:
<223> OTHER INFORMATION: Short artifical sequence for illustration
<220> FEATURE:
<221> NAME/KEY: misc_feature
<222> LOCATION: (1)..(1)
<223> OTHER INFORMATION: n at position 1 is the guanine's fluorescent
      analog 6-methyl-isoxanthopterin (6MI)
<220> FEATURE:
<221> NAME/KEY: misc_feature
<222> LOCATION: (6)..(6)
<223> OTHER INFORMATION: n at position 6 is the adenine's fluorescent
      analog 2-aminopurine (2AP).
<220> FEATURE:
<221> NAME/KEY: misc_feature
<222> LOCATION: (12)..(12)
<223> OTHER INFORMATION: n at position 12 is the cytosine's fluorescent
      analog pyrrolo-(d)C(Py).

<400> SEQUENCE: 3
ncattnattc gn                                                           12
```